(12) United States Patent
Yoshida et al.

(10) Patent No.: US 10,174,145 B1
(45) Date of Patent: Jan. 8, 2019

(54) METHACRYLIC RESIN

(71) Applicant: ASAHI KASEI KABUSHIKI KAISHA, Chiyoda-ku, Tokyo (JP)

(72) Inventors: Junichi Yoshida, Tokyo (JP); Harumi Watanabe, Tokyo (JP); Katsuhiro Iwase, Tokyo (JP); Keigo Sasaki, Tokyo (JP); Miyuki Kazunori, Tokyo (JP)

(73) Assignee: ASAHI KASEI KABUSHIKI KAISHA, Chiyoda-ku, Tokyo (JP)

( * ) Notice: Subject to any disclaimer, the term of this patent is extended or adjusted under 35 U.S.C. 154(b) by 0 days.

(21) Appl. No.: 15/880,480

(22) Filed: Jan. 25, 2018

(51) Int. Cl.
| | |
|---|---|
| C08F 220/46 | (2006.01) |
| C08F 220/18 | (2006.01) |
| C08F 220/14 | (2006.01) |
| C08L 33/10 | (2006.01) |
| G01N 21/31 | (2006.01) |
| G01N 30/00 | (2006.01) |

(52) U.S. Cl.
CPC .......... *C08F 220/46* (2013.01); *C08F 220/14* (2013.01); *C08F 220/18* (2013.01); *C08L 33/10* (2013.01); *C08F 2500/03* (2013.01); *C08L 2201/50* (2013.01); *G01N 2021/3155* (2013.01); *G01N 2030/486* (2013.01)

(58) Field of Classification Search
CPC .... C08F 220/46; C08F 220/14; C08F 220/18; C08F 2500/03; C08L 33/10; C08L 2201/50; G01N 2021/3155; G01N 2030/486
USPC .............................. 526/342, 317.1, 319, 269
See application file for complete search history.

(56) References Cited

U.S. PATENT DOCUMENTS

| | | | |
|---|---|---|---|
| 2013/0072651 A1 | 3/2013 | Yonemura et al. | |
| 2016/0325513 A1* | 11/2016 | Kamikariya | B29C 47/0004 |
| 2017/0031058 A1 | 2/2017 | Kitayama et al. | |

FOREIGN PATENT DOCUMENTS

| | | | |
|---|---|---|---|
| JP | H109151218 A | 6/1997 | |
| JP | H109324016 A | 12/1997 | |
| JP | 2001151814 A | 6/2001 | |
| JP | 2001233919 A | 8/2001 | |
| JP | 2003206303 A | 7/2003 | |
| JP | 2005281589 A | 10/2005 | |
| JP | 2008101203 A | 5/2008 | |
| JP | 2008191426 A | 8/2008 | |
| JP | 2009052021 A | 3/2009 | |
| JP | 2012132021 A | 7/2012 | |
| JP | 2012211279 A | 11/2012 | |
| JP | 2014028956 A | 2/2014 | |
| JP | 2014098117 A | 5/2014 | |
| JP | 2015105332 A | 6/2015 | |
| JP | 2015108161 A | 6/2015 | |
| JP | 2015135355 A | 7/2015 | |
| JP | 2017165939 A | 9/2017 | |
| WO | 2011149088 A1 | 12/2011 | |
| WO | 2015079694 A1 | 6/2015 | |

OTHER PUBLICATIONS

Jan. 17, 2017, Notification of Reasons for Refusal issued by the Japan Patent Office in the corresponding Japanese Patent Application No. 2016-235777.
Mar. 28, 2017, Notification of Reasons for Refusal issued by the Japan Patent Office in the corresponding Japanese Patent Application No. 2017-010193.
Written Opposition dated Jan. 10, 2018 against Japanese Patent Registration No. 6148802 (Opposition No. 2017-701189) issued by the Japan Patent Office with a partial English translation.
Written Opposition dated Nov. 2, 2017 against Japanese Patent Registration No. 6114459 (Opposition No. 2017-700981) issued by the Japan Patent Office with a partial English translation.

* cited by examiner

*Primary Examiner* — William K Cheung
(74) *Attorney, Agent, or Firm* — Kenja IP Law PC

(57) ABSTRACT

Methacrylic resin having high heat resistance, highly controlled birefringence, excellent color tone and transparency, and excellent moldability is provided. A methacrylic resin comprises a structural unit (B) having a cyclic structure-containing main chain, the structural unit (B) including at least one structural unit selected from the group consisting of an N-substituted maleimide-based structural unit (B-1) and a lactone ring structural unit (B-2), wherein a glass transition temperature is more than 120° C. and 160° C. or less, an amount of a methanol-soluble content is 5 mass % or less relative to 100 mass % of a total amount of the methanol-soluble content and a methanol-insoluble content in the methacrylic resin, and an yellowness index YI measured using a 10 cm optical path length cell for a 20 w/v % chloroform solution of the methanol-insoluble content is 0 to 7.

17 Claims, No Drawings

METHACRYLIC RESIN

TECHNICAL FIELD

This disclosure relates to methacrylic resin having high heat resistance, highly controlled birefringence, excellent color tone and transparency, and excellent moldability.

BACKGROUND

Methacrylic resins have excellent transparency, surface hardness, and so forth, and only display a small degree of the optical property of birefringence. For these reasons, methacrylic resin has been receiving attention as optical resin for optical material in various optical products such as flat panel displays, e.g. liquid crystal displays, plasma displays, and organic EL displays, small infrared sensors, fine optical waveguides, micro lenses, and DVD/Blu-ray Disc pickup lenses handling short-wavelength light, optical discs, optical films, and plastic substrates. The market for methacrylic resin is therefore expanding.

Particularly, methacrylic resin having a cyclic structure-containing main chain and compositions containing such methacrylic resin are known to have excellent performance in both heat resistance and optical property (e.g. see WO 2011/149088 A1 (PTL 1)), and the demand for them has been rapidly growing year by year. However, methacrylic resin having a cyclic structure-containing main chain and exhibiting improved heat resistance and optical property as mentioned above sometimes encounters problems such as coloring and decreased transmittance due to absorption of light in a visible light range caused by the ring structure or the like. In view of this, methods of reducing residual unreacted cyclic monomers in methacrylic resin have been disclosed in order to obtain methacrylic resin having a cyclic structure-containing main chain and exhibiting high transparency with little coloring.

For example, JP H9-324016 A (PTL 2) proposes a method of obtaining heat-resistant methacrylic resin having excellent transparency with little coloring by, in a manufacturing method of feeding a part of a monomer component including N-substituted maleimide (a) and methacrylic acid ester (b) to start polymerization and then feeding the remaining part of the monomer component during the polymerization, performing such control that causes the ratio of N-substituted maleimide (a) in the unreacted monomer component existing in the reaction system at the end of the feeding of the monomer component to be lower than the ratio of N-substituted maleimide (a) in the total feed of the monomer component, thus reducing residual N-substituted maleimide monomer content.

JP 2001-233919 A (PTL 3) proposes a method of suppressing coloring by, in a methacrylic acid ester-based monomer/maleimide monomer polymerization system using a sulfur-based chain transfer agent such as mercaptan, causing an acidic substance to exist in the reaction system, thus reducing a residual maleimide monomer and a maleimide monomer generated due to heating during molding processing or the like.

CITATION LIST

Patent Literatures

PTL 1: WO 2011/149088 A1
PTL 2: JP H9-324016 A
PTL 3: JP 2001-233919 A

SUMMARY

As the use of methacrylic resin has expanded from optical films to thicker molded products such as lenses and molded plates in recent years, resin exhibiting high transparency with little coloring even when used in, for example, a molded product having a long optical path length has been desired.

PTL 2 and PTL 3 each propose a coloring reduction method of, based on N-substituted maleimide having strong colorability as a monomer per se, reducing the amount of residual N-substituted maleimide in methacrylic resin or reducing the amount of N-substituted maleimide due to heat history in molding processing and the like.

However, their improvements in coloring degree and transparency are insufficient for methacrylic resin that can cope with the expansion of use to a molded product having a long optical path length.

There is thus a strong need to further improve the color tone and transparency of methacrylic resin based also on the polymer itself, rather than controlling only a coloring monomer such as residual N-substituted maleimide.

It could therefore be helpful to provide methacrylic resin having high heat resistance, highly controlled birefringence, excellent color tone and transparency, and excellent moldability.

As a result of conducting extensive research, we discovered that high transparency with little coloring can be achieved even in, for example, a molded product having a long optical path length, by fractionating methacrylic resin into methanol-soluble content and methanol-insoluble content and controlling the property of each fractionated component.

If the polymer itself can be improved, the polymer as methacrylic resin having a cyclic structure-containing main chain can be used not only as resin having an N-substituted maleimide monomer-derived ring structure but also as, for example, resin having a lactone ring structural unit.

The primary features of this disclosure are as follows.

[1] A methacrylic resin comprising
a structural unit (B) having a cyclic structure-containing main chain, the structural unit (B) including at least one structural unit selected from the group consisting of an N-substituted maleimide-based structural unit (B-1) and a lactone ring structural unit (B-2), wherein
a glass transition temperature is more than 120° C. and 160° C. or less,
an amount of a methanol-soluble content is 5 mass % or less relative to 100 mass % of a total amount of the methanol-soluble content and a methanol-insoluble content in the methacrylic resin, and
an yellowness index YI measured using a 10 cm optical path length cell for a 20 w/v % chloroform solution of the methanol-insoluble content is 0 to 7.

[2] The methacrylic resin according to the foregoing [1], wherein
a transmittance in 680 nm as measured using the 10 cm optical path length cell for the 20 w/v % chloroform solution of the methanol-insoluble content is 90% or more.

[3] The methacrylic resin according to the foregoing [1] or [2], comprising 50 mass % to 97 mass % of a methacrylic acid ester monomer unit (A), relative to 100 mass % of the methacrylic resin.

[4] The methacrylic resin according to any one of the foregoing [1] to [3], comprising 3 mass % to 30 mass % of the structural unit (B) having a cyclic structure-containing main chain, and 0 mass % to 20 mass % of an other vinyl-based monomer unit (C) copolymerizable with a methacrylic acid ester monomer, relative to 100 mass % of the methacrylic resin.

[5] The methacrylic resin according to any one of the foregoing [1] to [4], wherein the structural unit (B) is contained in an amount of 45 mass % to 100 mass % relative to 100 mass %, in total, of the structural unit (B) and the monomer unit (C).

[6] The methacrylic resin according to any one of the foregoing [1] to [5], wherein the monomer unit (C) includes at least one structural unit selected from the group consisting of an acrylic acid ester monomer, an aromatic vinyl-based monomer, and a vinyl cyanide-based monomer.

[7] The methacrylic resin according to any one of the foregoing [1] to [6], having a photoelastic coefficient of $-2\times10^{-12}$ Pa$^{-1}$ to $+2\times10^{-12}$ Pa$^{-1}$.

[8] The methacrylic resin according to any one of the foregoing [1] to [7], having a ratio Mz/Mw of a Z-average molecular weight Mz to a weight-average molecular weight Mw of 1.3 to 2.0 as measured by gel permeation chromatography (GPC).

According to this disclosure, it is thus possible to provide methacrylic resin having high heat resistance, highly controlled birefringence, excellent color tone and transparency, and excellent moldability.

DETAILED DESCRIPTION

The following provides a detailed description of an embodiment of the present disclosure (hereinafter, also referred to as the "present embodiment"). However, the present disclosure is not limited by the following description and may be implemented with various modifications within the essential scope thereof.

(Methacrylic Resin)

Methacrylic resin in the present embodiment includes a methacrylic acid ester monomer unit (A) and a structural unit (B) having at least one cyclic structure-containing main chain selected from the group consisting of an N-substituted maleimide monomer-derived structural unit (B-1) and a lactone ring structural unit (B-2), and optionally selectively includes other vinyl-based monomer unit (C) copolymerizable with the methacrylic acid ester monomer.

Each monomer structural unit is described below.

—Methacrylic Acid Ester Monomer-Derived Structural Unit (A)—

First, the methacrylic acid ester monomer-derived structural unit (A) is described.

The methacrylic acid ester monomer-derived structural unit (A) is, for example, formed from a monomer selected from the following methacrylic acid esters. Examples of methacrylic acid esters that can be used include methyl methacrylate, ethyl methacrylate, n-propyl methacrylate, isopropyl methacrylate, n-butyl methacrylate, isobutyl methacrylate, t-butyl methacrylate, 2-ethylhexyl methacrylate, cyclopentyl methacrylate, cyclohexyl methacrylate, cyclooctyl methacrylate, tricyclodecyl methacrylate, dicyclooctyl methacrylate, tricyclododecyl methacrylate, isobornyl methacrylate, phenyl methacrylate, benzyl methacrylate, 1-phenylethyl methacrylate, 2-phenoxyethyl methacrylate, 3-phenylpropyl methacrylate, and 2,4,6-tribromophenyl methacrylate.

One of these monomers may be used individually, or two or more of these monomers may be used together.

Of these methacrylic acid esters, methyl methacrylate and benzyl methacrylate are preferable in terms of providing the resultant methacrylic resin with excellent transparency and weather resistance.

The methacrylic resin may include just one type of methacrylic acid ester monomer-derived structural unit (A) or may include two or more types of methacrylic acid ester monomer-derived structural units (A).

The content of the methacrylic acid ester monomer-derived structural unit (A) is preferably 50 mass % to 97 mass %, more preferably 55 mass % to 97 mass %, further preferably 55 mass % to 95 mass %, still more preferably 60 mass % to 93 mass %, and particularly preferably 60 mass % to 90 mass % relative to 100 mass % of the methacrylic resin, in terms of imparting sufficient heat resistance to the methacrylic resin by the below-mentioned structural unit (B) having a cyclic structure-containing main chain.

The following describes the structural unit (B) having a cyclic structure-containing main chain.

—N-Substituted Maleimide Monomer-Derived Structural Unit (B-1)—

Next, an N-substituted maleimide monomer-derived structural unit (B-1) is described.

The N-substituted maleimide monomer-derived structural unit (B-1) may be formed from at least one selected from a monomer represented by the following formula (1) and/or a monomer represented by the following formula (2), and is preferably formed from both a monomer represented by the following formula (1) and a monomer represented by the following formula (2).

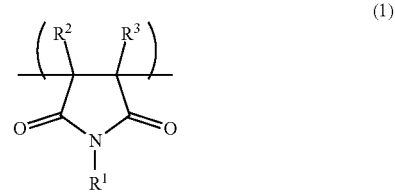

(1)

In formula (1), $R^1$ represents an arylalkyl group having a carbon number of 7 to 14 or an aryl group having a carbon number of 6 to 14, and $R^2$ and $R^3$ each represent, independently of one another, a hydrogen atom, an alkyl group having a carbon number of 1 to 12, or an aryl group having a carbon number of 6 to 14.

Note that in a situation in which $R^2$ is an aryl group, $R^2$ may include a halogen as a substituent.

Moreover, $R^1$ may be substituted with a substituent such as a halogen atom, an alkyl group having carbon number of 1 to 6, an alkoxy group having a carbon number of 1 to 6, a nitro group, or a benzyl group.

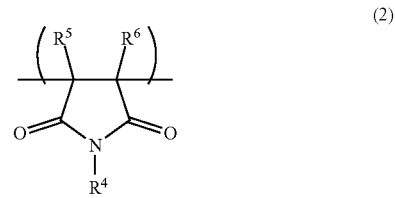

(2)

In formula (2), $R^4$ represents a hydrogen atom, a cycloalkyl group having a carbon number of 3 to 12, or an alkyl group having a carbon number of 1 to 12, and $R^5$ and $R^6$ each represent, independently of one another, a hydrogen atom, an alkyl group having a carbon number of 1 to 12, or an aryl group having a carbon number of 6 to 14.

Specific examples are listed below.

Examples of monomers represented by formula (1) include N-phenylmaleimide, N-benzylmaleimide, N-(2-chlorophenyl)maleimide, N-(4-chlorophenyl)maleimide, N-(4-bromophenyl)maleimide, N-(2-methylphenyl)maleimide, N-(2-ethylphenyl)maleimide, N-(2-methoxyphenyl)maleimide, N-(2-nitrophenyl)maleimide, N-(2,4,6-trimethylphenyl)maleimide, N-(4-benzylphenyl)maleimide, N-(2,4,6-tribromophenyl)maleimide, N-naphthylmaleimide, N-anthracenylmaleimide, 3-methyl-1-phenyl-1H-pyrrole-2,5-dione, 3,4-dimethyl-1-phenyl-1H-pyrrole-2,5-dione, 1,3-diphenyl-1H-pyrrole-2,5-dione, and 1,3,4-triphenyl-1H-pyrrole-2,5-dione.

Of these monomers, N-phenylmaleimide and N-benzylmaleimide are preferable in terms of providing the resultant methacrylic resin with excellent heat resistance and optical properties such as birefringence.

One of these monomers may be used individually, or two or more of these monomers may be used together.

Examples of monomers represented by formula (2) include N-methylmaleimide, N-ethylmaleimide, N-n-propylmaleimide, N-isopropylmaleimide, N-n-butylmaleimide, N-isobutylmaleimide, N-s-butylmaleimide, N-t-butylmaleimide, N-n-pentylmaleimide, N-n-hexylmaleimide, N-n-heptylmaleimide, N-n-octylmaleimide, N-laurylmaleimide, N-stearylmaleimide, N-cyclopentylmaleimide, N-cyclohexylmaleimide, 1-cyclohexyl-3-methyl-1-phenyl-1H-pyrrole-2,5-dione, 1-cyclohexyl-3,4-dimethyl-1-phenyl-1H-pyrrole-2,5-dione, 1-cyclohexyl-3-phenyl-1H-pyrrole-2,5-dione, and 1-cyclohexyl-3,4-diphenyl-1H-pyrrole-2,5-dione.

Of these monomers, N-methylmaleimide, N-ethylmaleimide, N-isopropylmaleimide, and N-cyclohexylmaleimide are preferable in terms of providing the resultant methacrylic resin with excellent weather resistance, and N-cyclohexylmaleimide is particularly preferable in terms of providing excellent low water absorbency demanded of optical materials in recent years.

One of these monomers may be used individually, or two or more of these monomers may be used together.

The methacrylic resin according to the present embodiment is particularly preferably obtained using a monomer represented by formula (1) and a monomer represented by formula (2), in combination, in order to exhibit a high level of control on birefringence properties.

The content (B1) of a structural unit derived from the monomer represented by formula (1), in terms of a molar ratio (B1/B2) relative to the content (B2) of a structural unit derived from the monomer represented by formula (2), is preferably greater than 0 and no greater than 15, and more preferably greater than 0 and no greater than 10.

When the molar ratio (B1/B2) is within any of the ranges set forth above, the methacrylic resin according to the present embodiment can display good heat resistance and good photoelastic properties while maintaining transparency, and without yellowing or loss of environmental resistance.

The content of the N-substituted maleimide monomer-derived structural unit (B-1) is not specifically limited so long as the resultant composition satisfies the glass transition temperature range according to the present embodiment. However, the content of the N-substituted maleimide monomer-derived structural unit relative to 100 mass % of the methacrylic resin is preferably 5 mass % to 40 mass %, and more preferably 5 mass % to 35 mass %.

When the content of the N-substituted maleimide monomer-derived structural unit is within any of the ranges set forth above, a more adequate enhancement effect can be achieved with respect to heat resistance of the methacrylic resin, and a more preferable enhancement effect can also be achieved with respect to weather resistance, low water absorbency, and optical properties of the methacrylic resin. Restricting the content of the N-substituted maleimide monomer-derived structural unit to 40 mass % or less is effective for preventing a decrease in physical properties of the methacrylic resin caused by a large amount of monomer remaining unreacted due to reduced reactivity of monomer components in the polymerization reaction.

—Lactone Ring Structural Unit (B-2)—

The methacrylic resin having the lactone ring structural unit in the main chain can be, for example, formed by a method described in JP 2001-151814 A, JP 2004-168882 A, JP 2005-146084 A, JP 2006-96960 A, JP 2006-171464 A, JP 2007-63541 A, JP 2007-297620 A, or JP 2010-180305 A.

The lactone ring structural unit included in the methacrylic resin in the present embodiment may be formed after resin polymerization.

The lactone ring structural unit in the present embodiment is preferably a six-membered ring, for excellent stability of the ring structure.

For example, the lactone ring structural unit which is a six-membered ring particularly preferably has the structure expressed by the following general formula (3).

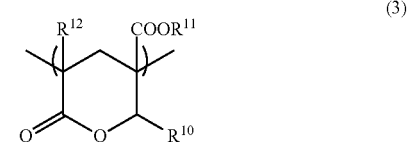

In general formula (3), $R^{10}$, $R^{11}$, and $R^{12}$ each independent represent a hydrogen atom or an organic residue with a carbon number of 1 to 20.

Examples of the organic residue include: unsaturated aliphatic hydrocarbon groups (alkenyl group, etc.) with a carbon number of 2 to 20 such as methyl group, ethyl group, and propyl group; unsaturated aliphatic hydrocarbon groups (alkenyl group, etc.) with a carbon number of 2 to 20 such as ethenyl group and propenyl group; aromatic hydrocarbon groups (aryl group, etc.) with a carbon number of 6 to 20 such as phenyl group and naphthyl group; and groups obtained by substituting one or more hydrogen atoms in such saturated aliphatic hydrocarbon groups, unsaturated aliphatic hydrocarbon groups, or aromatic hydrocarbon groups with at least one group selected from the group consisting of hydroxy group, carboxyl group, ether group, and ester group.

For example, the lactone ring structure can be formed by, after copolymerizing an acrylate monomer having a hydroxy group and a methacrylic acid ester monomer such as methyl methacrylate and introducing the hydroxy group and the ester group or carboxyl group into the molecular chain, causing dealcoholization (esterification) or dehydration condensation (hereafter also referred to as "cyclization condensation reaction") between the hydroxy group and the ester group or carboxyl group.

Examples of the acrylate monomer having the hydroxy group used in polymerization include 2-(hydroxymethyl) acrylate, 2-(hydroxyethyl)acrylate, 2-(hydroxymethyl)alkyl acrylate (e.g. 2-(hydroxymethyl)methyl acrylate, 2-(hydroxymethyl)ethyl acrylate, 2-(hydroxymethyl)isopropyl acrylate, 2-(hydroxymethyl)n-butyl acrylate, 2-(hydroxymethyl)t-butyl acrylate), and 2-(hydroxyethyl)alkyl acrylate. 2-(hydroxymethyl)acrylate and 2-(hydroxymethyl)alkyl acrylate which are each a monomer having a hydroxyaryl site are preferable, and 2-(hydroxymethyl)methyl acrylate and 2-(hydroxymethyl)ethyl acrylate are particularly preferable.

The content of the lactone ring structural unit in the methacrylic resin having the lactone ring structural unit in the main chain is not limited as long as it satisfies the preferable glass transition temperature range of the methacrylic resin in the present embodiment. The content of the lactone ring structural unit is preferably 5 mass % to 40 mass % and more preferably 5 mass % to 35 mass %, relative to 100 mass % of the methacrylic resin.

If the content of the lactone ring structural unit is in this range, the ring structure introduction effects such as solvent resistance improvement and surface hardness improvement can be developed while maintaining molding process ability.

The content of the lactone ring structure in the methacrylic resin can be determined using the method described in any of the foregoing patent documents.

The content of the structural unit (B) having a cyclic structure-containing main chain is preferably 3 mass % to 40 mass % relative to 100 mass % of the methacrylic resin, in terms of the heat resistance, heat stability, strength, and flowability of the methacrylic resin in the present embodiment. The content of the structural unit (B) is more preferably 5 mass % or more, further preferably 7 mass % or more, and still more preferably 8 mass % or more. The content of the structural unit (B) is more preferably 30 mass % or less, further preferably 28 mass % or less, still more preferably 25 mass % or less, particularly preferably 20 mass % or less, still further preferably 18 mass % or less, and most preferably less than 15 mass %.

—Other Vinyl-Based Monomer Unit (C) Copolymerizable with Methacrylic Acid Ester Monomer—

Examples of the other vinyl-based monomer unit (C) (hereafter also referred to as "monomer unit (C)") copolymerizable with the methacrylic acid ester monomer, which may constitute the methacrylic resin in the present embodiment, include an aromatic vinyl-based monomer unit (C-1), an acrylic acid ester monomer unit (C-2), a vinyl cyanide-based monomer unit (C-3), and a monomer unit (C-4) other than these.

The other vinyl-based monomer units (C) copolymerizable with the methacrylic acid ester monomer may be used singly or in combination of two or more types.

The monomer unit (C) may be selected as appropriate depending on the properties required of the methacrylic resin in the present embodiment. In the case where properties such as heat stability, flowability, mechanical property, and chemical resistance are particularly required, at least one type selected from the group consisting of the aromatic vinyl-based monomer unit (C-1), the acrylic acid ester monomer unit (C-2), and the vinyl cyanide-based monomer unit (C-3) is suitable.

[Aromatic Vinyl-Based Monomer Unit (C-1)]

A monomer forming the aromatic vinyl-based monomer unit (C-1) constituting the methacrylic resin in the present embodiment is not limited, but is preferably an aromatic vinyl-based monomer expressed by the following general formula (4).

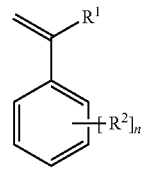

In general formula (4), $R^1$ represents a hydrogen atom or an alkyl group with a carbon number of 1 to 6. The alkyl group may be, for example, substituted by a hydroxyl group.

$R^2$ is selected from the group consisting of a hydrogen atom, an alkyl group with a carbon number of 1 to 12, an alkoxy group with a carbon number of 1 to 12, an aryl group with a carbon number of 6 to 8, and an aryloxy group with a carbon number of 6 to 8. $R^2$ may all be the same group, or different groups. $R^2$ together may form a ring structure.

n represents an integer of 0 to 5.

Non-limiting examples of the monomer expressed by general formula (4) include styrene, o-methylstyrene, m-methylstyrene, p-methylstyrene, 2,4-dimethylstyrene, 2,5-dimethylstyrene, 3,4-dimethylstyrene, 3,5-dimethylstyrene, p-ethylstyrene, m-ethylstyrene, o-ethylstyrene, p-tert-butylstyrene, 1-vinylnaphthalene, 2-vinylnaphthalene, 1,1-diphenylethylene, isopropenylbenzene(α-methylstyrene), isopropenyltoluene, isopropenylethylbenzene, isopropenylpropylbenzene, isopropenylbutylbenzene, isopropenylpentylbenzene, isopropenylhexylbenzene, isopropenyloctylbenzene, α-hydroxymethylstyrene, and α-hydroxyethylstyrene.

Of these, styrene and isopropenylbenzene are preferable. Styrene is more preferable, in terms of providing flowability, reducing unreacted monomers by improving the polymerization conversion rate, and the like.

These may be selected as appropriate depending on the required properties in the methacrylic resin in the present embodiment.

In the case of using the aromatic vinyl-based monomer unit (C-1), the content is preferably 23 mass % or less, more preferably 20 mass % or less, further preferably 18 mass % or less, still more preferably 15 mass % or less, and still further preferably 10 mass % or less relative to 100 mass % of the total amount of the monomer unit (A) and the structural unit (B), in terms of the balance between heat resistance, residual monomer reduction, and flowability.

In the case of using the aromatic vinyl-based monomer unit (C-1) together with the maleimide-based structural unit (B-1), the ratio (mass ratio) (i.e. (C-1) content/(B-1) content) of the content of the monomer unit (C-1) to the content of the structural unit (B-1) is preferably 0.3 to 5, in terms of processing flowability when molding a film, silver streak reduction by residual monomer reduction, and the like.

In terms of maintaining favorable color tone and heat resistance, the ratio is preferably 5 or less, more preferably 3 or less, and further preferably 1 or less. In terms of residual monomer reduction, the ratio is preferably 0.3 or more, and more preferably 0.4 or more.

These aromatic vinyl-based monomers (C-1) may be used singly or in combination of two or more types.

[Acrylic Acid Ester Monomer Unit (C-2)]

A monomer forming the acrylic acid ester monomer unit (C-2) constituting the methacrylic resin in the present embodiment is not limited, but is preferably an acrylic acid ester monomer expressed by the following general formula (5).

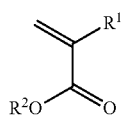

In general formula (5), $R^1$ represents a hydrogen atom or an alkoxy group with a carbon number of 1 to 12, and $R^2$ represents an alkyl group with a carbon number of 1 to 18.

As the monomer for forming the acrylic acid ester monomer unit (C-2), in terms of enhancing weather resistance, heat resistance, flowability, and heat stability in the methacrylic resin for films in the present embodiment, methyl acrylate, ethyl acrylate, n-propyl acrylate, isopropyl acrylate, n-butyl acrylate, sec-butyl acrylate, 2-ethylhexyl acrylate, cyclohexyl acrylate, phenyl acrylate, and the like are preferable, and methyl acrylate, ethyl acrylate, and n-butyl acrylate are more preferable. In terms of availability, methyl acrylate and ethyl acrylate are further preferable.

These acrylic acid ester monomer units (C-2) may be used singly or in combination of two or more types.

In the case of using the acrylic acid ester monomer unit (C-2), the content is preferably 5 mass % or less and more preferably 3 mass % or less relative to 100 mass % of the total amount of the monomer unit (A) and the structural unit (B), in terms of heat resistance and heat stability.

[Vinyl Cyanide-Based Monomer Unit (C-3)]

A monomer forming the vinyl cyanide-based monomer unit (C-3) constituting the methacrylic resin in the present embodiment is not limited. Examples of the monomer include acrylonitrile, methacrylonitrile, ethacrylonitrile, and vinylidene cyanide. In terms of availability and chemical resistance, acrylonitrile is preferable.

These vinyl cyanide-based monomer units (C-3) may be used singly or in combination of two or more types.

In the case of using the vinyl cyanide-based monomer unit (C-3), the content is preferably 15 mass % or less, more preferably 12 mass % or less, and further preferably 10 mass % or less relative to 100 mass % of the total amount of the monomer unit (A) and the structural unit (B), in terms of maintaining solvent resistance and heat resistance.

[Monomer Unit (C-4) Other than (C-1) to (C-3)]

A monomer forming the monomer unit (C-4) other than (C-1) to (C-3) constituting the methacrylic resin in the present embodiment is not limited. Examples of the monomer include: amides such as acrylamide and methacrylamide; glycidyl compounds such as glycidyl(meth)acrylate and arylglycidylether; unsaturated carboxylic acids such as acrylic acid, methacrylic acid, itaconic acid, maleic acid, and fumaric acid, and half esters or anhydrides thereof; unsaturated alcohols such as methallyl alcohol and allyl alcohol; olefins such as ethylene, propylene, and 4-methyl-1-pentene; and other vinyl compounds or vinylidene compounds such as vinyl acetate, 2-hydroxymethyl-1-butene, methylvinylketone, N-vinylpyrrolidone, and N-vinylcarbazole.

Examples of a crosslinkable compound having a plurality of reaction double bonds include: compounds obtained by esterificating, by acrylic acid or methacrylic acid, both terminal hydroxyl groups of ethyleneglycols such as ethyleneglycol di(meth)acrylate, diethyleneglycol di(meth)acrylate, triethyleneglycol di(meth)acrylate, and tetraethyleneglycol di(meth)acrylate or oligomers thereof; compounds obtained by esterificating, by acrylic acid or methacrylic acid, two alcohol hydroxyl groups of neopentylglycol di(meth)acrylate, di(meth)acrylate, and the like; compounds obtained by esterificating, by acrylic acid or methacrylic acid, polyhydric alcohol derivative such as trimethylolpropane and pentaerythritol; polyfunctional monomers such as divinylbenzene.

Of the above-mentioned monomers constituting the monomer unit (C), at least one type selected from the group consisting of methyl acrylate, ethyl acrylate, styrene, and acrylonitrile is preferable in terms of availability.

The content of the other vinyl-based monomer unit (C) copolymerizable with the methacrylic acid ester monomer is 0 mass % to 20 mass %, preferably 0 mass % to 18 mass %, and more preferably 0 mass % to 15 mass % relative to 100 mass % of the methacrylic resin, in terms of enhancing the effect of imparting heat resistance by the structural unit (B).

Particularly in the case where crosslinkable polyfunctional (meth)acrylate having a plurality of reaction double bonds is used as the monomer unit (C), the content of the monomer unit (C) is preferably 0.5 mass % or less, more preferably 0.3 mass % or less, and further preferably 0.2 mass % or less, in terms of polymer flowability.

In particular, in the present embodiment, the content of the structural unit (B) is 45 mass % to 100 mass % relative to 100 mass % of the total amount of the structural unit (B) and the monomer unit (C), in terms of the heat resistance and optical property of the methacrylic resin. Here, the content of the structural unit (C) is 0 mass % to 55 mass %. The content of the structural unit (B) is preferably 50 mass % to 100 mass %, more preferably 50 mass % to 90 mass %, and further preferably 50 mass % to 80 mass %.

The properties of the methacrylic resin in the present embodiment are described below.

The glass transition temperature (Tg) of the methacrylic resin in the present embodiment is more than 120° C. and 160° C. or less.

If the glass transition temperature of the methacrylic resin is more than 120° C., sufficient heat resistance necessary for lens molded products and liquid crystal display film molded product optical films in recent years can be achieved more easily. In terms of dimensional stability at use environment temperature, the glass transition temperature (Tg) is more preferably 125° C. or more, and further preferably 130° C. or more.

If the glass transition temperature (Tg) of the methacrylic resin is 160° C. or less, melt processing at extremely high temperature can be avoided to suppress thermal decomposition of the resin and the like, with it being possible to obtain a favorable product. For these reasons, the glass transition temperature (Tg) is preferably 150° C. or less.

The glass transition temperature (Tg) can be determined through measurement according to JIS-K7121. The glass transition temperature (Tg) can be specifically measured by the method described in the below-mentioned Examples.

The ratio of the amount of methanol-soluble content to 100 mass % of the total amount of methanol-soluble content and methanol-insoluble content in the methacrylic resin in the present embodiment is 5 mass % or less, preferably 4.5 mass % or less, further preferably 4 mass % or less, still more preferably 3.5 mass % or less, still further preferably 3 mass % or less, and still further preferably 2.5 mass % or less. The ratio is preferably more than 0 mass %, further preferably more than 0.1 mass %, still more preferably more than 0.2 mass %, still further preferably more than 0.3 mass %.

By setting the ratio of the amount of soluble matter to 5 mass % or less, troubles during molding such as casting roll stain in film molding and silver streaks in injection molding can be suppressed.

The methanol-soluble content and the methanol-insoluble content are obtained by, after making the methacrylic resin into a chloroform solution, dropping the solution into methanol to cause reprecipitation, separating a filtrate and a filtration residue, and then drying the obtained filtrate and filtration residue. The methanol-soluble content and the methanol-insoluble content can be specifically obtained by the method described in the below-mentioned Examples.

In the methacrylic resin in the present embodiment, the yellowness index (YI) measured using a 10 cm optical path length cell for a 20 w/v % chloroform solution of the methanol-insoluble content is 0 to 7, preferably 0.5 to 6, more preferably 0.8 to 5, and further preferably 1 to 4.

In the methacrylic resin in the present embodiment, the transmittance in 680 nm measured under the same condition as the above-mentioned YI measurement is preferably 90% or more, more preferably 91% or more, and further preferably 92% or more.

If the yellowness index (YI) and the transmittance are in the respective ranges, a molded product suitable for optical use can be obtained.

The yellowness index (YI) and the transmittance can be specifically measured by the method described in the below-mentioned Examples.

In the methacrylic resin in the present embodiment, the weight-average molecular weight (Mw) in terms of polymethyl methacrylate measured by gel permeation chromatography (GPC) is preferably in a range of 65,000 to 300,000, more preferably in a range of 100,000 to 220,000, and further preferably in a range of 120,000 to 180,000.

If the weight-average molecular weight (Mw) is in this range, excellent balance between mechanical strength and flowability can be achieved.

Regarding the ratios between the Z-average molecular weight (Mz), the weight-average molecular weight (Mw), and the number-average molecular weight (Mn) as parameters indicating the molecular weight distribution, in terms of the balance between flowability and mechanical strength in the methacrylic resin in the present embodiment, Mw/Mn is preferably 1.5 to 3.0, more preferably 1.6 to 2.5, and further preferably 1.6 to 2.3. Mz/Mw is preferably 1.3 to 2.0, more preferably 1.3 to 1.8, and further preferably 1.4 to 1.7.

Particularly, if Mz/Mw is in this range, methacrylic resin having excellent color tone can be obtained.

The Z-average molecular weight, weight-average molecular weight, and number-average molecular weight of the methacrylic resin can be specifically measured by the method described in the below-mentioned Examples.

The absolute value of the photoelastic coefficient $C_R$ of the methacrylic resin that includes the structural unit (X) having a cyclic structure-containing main chain in the present embodiment is preferably $3.0 \times 10^{-12}$ $Pa^{-1}$ or less, more preferably $2.0 \times 10^{-12}$ $Pa^{-1}$ or less, and further preferably $1.0 \times 10^{-12}$ $Pa^{-1}$ or less.

The photoelastic coefficient is described in various documents (e.g. Kagaku Sosetsu, No. 39, 1998 (Gakkai Shuppan Center)), and is defined by the following Formulas (i-a) and (i-b). It can be understood that, when the photoelastic coefficient $C_R$ is closer to zero, the birefringence change by an external force is smaller.

$$C_R = |\Delta n|/\sigma_R \quad \text{(i-a)}$$

$$|\Delta n| = |n_x - n_y| \quad \text{(i-b)}$$

(In the formulas, $C_R$ is the photoelastic coefficient, $\sigma_R$ is the stretching stress, $|\Delta n|$ is the absolute value of birefringence, $n_x$ is the refractive index in the stretching direction, and $n_y$ is the refractive index in the direction perpendicular to the stretching direction in plane.)

If the absolute value of the photoelastic coefficient $C_R$ of the methacrylic resin in the present embodiment is $3.0 \times 10^{-12}$ $Pa^{-1}$ or less, when the resin is made into a film and used in a liquid crystal display device, phase difference unevenness, lower contrast in a display screen peripheral part, and light leakage can be reduced or prevented.

The photoelastic coefficient $C_R$ of the methacrylic resin can be specifically measured by the method described in the below-mentioned Examples.

(Methacrylic Resin Manufacturing Method)

The method of manufacturing the methacrylic resin in the present embodiment is described below.

Examples of the method of manufacturing the methacrylic resin in the present embodiment include the following manufacturing methods of first and second modes.

In the first mode, in a method of batch or semibatch radical polymerization of two or more monomers including the methacrylic acid ester monomer in a solvent, a radical polymerization initiator whose half-life at the polymerization temperature is 1 min or more and less than 60 min is used. The radical polymerization initiator is added into a reactor while gradually decreasing the additive amount per unit time, to promote the polymerization of the monomers. Here, the additive amount of the radical polymerization initiator added after the polymerization conversion rate reaches 85% is 10 mass % to 25 mass % relative to 100 mass % of the total additive amount of the radical polymerization initiator.

In the first mode, the radical polymerization initiator may be added continuously or intermittently. In the case of adding the radical polymerization initiator intermittently, the additive amount per unit time does not involve the time during which the radical polymerization initiator is not added.

In the second mode, in a method of batch or semibatch radical polymerization of two or more monomer components including the methacrylic acid ester monomer in a solvent, a radical polymerization initiator whose half-life at the polymerization temperature is 60 min or more is used. Within 30 min from the addition start of the polymerization initiator, 25 mass % or more of the total additive amount of the radical polymerization initiator is added. After 30 min from the addition start of the polymerization initiator, 25 mass % or more of the total additive amount of the monomers is added.

In the case where the temperature varies during polymerization, the time average of the polymerization temperature until the polymerization conversion rate reaches 95% is regarded as the polymerization temperature.

The method of manufacturing the methacrylic resin including the N-substituted maleimide-based structural unit (B-1) as the structural unit (B) having a cyclic structure-containing main chain is described in detail below.

As the method of manufacturing the methacrylic resin having the N-substituted maleimide monomer-derived structural unit (B-1) in the main chain in the present embodiment, a solution polymerization method is used.

In the manufacturing method in the present embodiment, a polymerization type may be batch or semibatch. Batch is a process of, after charging the total amount of raw material into a reactor, starting and promoting reaction and, after the reaction ends, recovering the product. Semibatch is a process of simultaneously performing one of the raw material charging and the product recovery during the progress of the reaction. As the method of manufacturing the methacrylic resin having the N-substituted maleimide monomer-derived structural unit in the main chain in the present embodiment, semibatch in which part of the raw material is charged after the reaction start is preferable.

In the manufacturing method in the present embodiment, monomer polymerization by radical polymerization is employed.

No specific limitations are placed on the polymerization solvent that is used so long as the solubility of the maleimide copolymer obtained through polymerization is high and an appropriate reaction liquid viscosity can be maintained in order to prevent gelation or the like.

Specific examples of polymerization solvents that can be used include aromatic hydrocarbons such as toluene, xylene, ethylbenzene, and isopropylbenzene; ketones such as methyl isobutyl ketone, butyl cellosolve, methyl ethyl ketone, and cyclohexanone; and polar solvents such as dimethylformamide and 2-methylpyrrolidone.

Moreover, an alcohol such as methanol, ethanol, or isopropanol may be used in combination as the polymerization solvent to the extent that dissolution of the polymerized product during polymerization is not impaired.

No specific limitations are placed on the amount of solvent used in polymerization so long as polymerization proceeds, precipitation of the copolymer or used monomers does not occur in production, and the solvent can be easily removed. For example, when the total amount of used monomers is taken to be 100 parts by mass, the amount of solvent is preferably 10 parts by mass to 200 parts by mass. The amount of solvent is more preferably 25 parts by mass to 200 parts by mass, further preferably 50 parts by mass to 200 parts by mass, and even more preferably 50 parts by mass to 150 parts by mass.

The polymerization temperature is not limited as long as it is a temperature at which polymerization proceeds. The polymerization temperature is preferably 70° C. to 180° C., more preferably 80° C. to 160° C., further preferably 90° C. to 150° C., and still more preferably 100° C. to 150° C. In terms of productivity, the polymerization temperature is preferably 70° C. or more. To suppress side reaction in the polymerization and obtain a polymer having a desired molecular weight and quality, the polymerization temperature is preferably 180° C. or less.

The polymerization time is not limited as long as it is a time in which a necessary polymerization degree can be achieved at a necessary conversion rate. In terms of productivity and the like, the polymerization time is preferably 2 hours to 15 hours, more preferably 3 hours to 12 hours, and further preferably 4 hours to 10 hours.

The polymerization conversion rate at the polymerization end of the methacrylic resin having the N-substituted maleimide monomer-derived structural unit in the main chain in the present embodiment is preferably 93% to 99.9%, more preferably 95% to 99.5%, and further preferably 97% to 99%.

The polymerization conversion rate is the ratio of the value obtained by subtracting the total mass of the residual monomer at the polymerization end from the total mass of the monomer added in the polymerization system, to the total mass of the monomer added in the polymerization system.

The amount of the residual N-substituted maleimide monomer in the solution after the polymerization (N-substituted maleimide residual amount) is preferably 100 mass ppm to 7000 mass ppm, more preferably 200 mass ppm to 5000 mass ppm, and further preferably 300 mass ppm to 3000 mass ppm.

When the polymerization conversion rate is higher and the N-substituted maleimide residual amount is smaller, less monomer is involved in the solvent recovery system. This reduces the load on the purified system, and is economical as the original unit increases. However, if the polymerization conversion rate is excessively high or the N-substituted maleimide residual amount is excessively low, there is a possibility that the amount of coloring low molecular weight component and the amount of methanol-soluble content increase and color tone and molding processability are adversely affected.

In polymerization reaction, a chain transfer agent may be added according to need.

The chain transfer agent may be a chain transfer agent typically used in radical polymerization. Examples of the chain transfer agent include: mercaptan compounds such as n-butylmercaptan, n-octylmercaptan, n-decylmercaptan, n-dodecylmercaptan, and 2-ethylhexyl thioglycolate; halogen compounds such as carbon tetrachloride, methylene chloride, and bromoform; and unsaturated hydrocarbon compounds such as α-methylstyrene dimer, α-terpinene, dipentene, and terpinolene.

These may be used singly or in combination of two or more types.

The chain transfer agent may be added at any stage while polymerization reaction is in progress, and so the addition timing is not limited.

The additive amount of the chain transfer agent may be 0.01 parts to 1 parts by mass and preferably 0.05 parts to 0.5 parts by mass, relative to 100 parts by mass of the total amount of the monomers used in polymerization.

In solution polymerization, it is important to reduce the dissolved oxygen concentration in the polymerization solution as much as possible. For example, the dissolved oxygen concentration is preferably 10 ppm or less.

The dissolved oxygen concentration can be measured using, for example, a dissolved oxygen analyzer DO meter B-505 (made by Iijima Electronic Co., Ltd.). As the method of decreasing the dissolved oxygen concentration, a method such as: bubbling inert gas in the polymerization solution; repeatedly performing an operation of increasing pressure in a container containing the polymerization solution to about 0.2 MPa using inert gas and then discharging the pressure before polymerization; or passing inert gas into the container containing the polymerization solution may be selected as appropriate.

In polymerization reaction, a polymerization initiator is added.

The polymerization initiator may be any initiator typically used in radical polymerization. Examples of the polymerization initiator include: organic peroxides such as cumene hydroperoxide, diisopropylbenzene hydroperoxide, di-t-butyl peroxide, lauroyl peroxide, benzoyl peroxide, t-butylperoxyisopropylcarbonate, t-amyl peroxy-2-ethylhexanoate, t-amyl peroxyisononanoate, and 1,1-di-t-butylperoxycyclohexane; and azo compounds such as 2,2'-azobis(isobutyronitrile), 1,1'-azobis(cyclohexanecarbonitrile), 2,2'-azobis(2,4-dimethylvaleronitrile), and dimethyl-2,2'-azobisisobutylate.

These may be used singly or in combination of two or more types.

Such polymerization initiator may be added at any stage while polymerization reaction is in progress.

The additive amount of the polymerization initiator may be 0.01 parts to 1 parts by mass and preferably 0.05 parts to 0.5 parts by mass, relative to 100 parts by mass of the total amount of the monomers used in polymerization.

In the polymerization of the methacrylic resin having the N-substituted maleimide monomer-derived ring structural unit in the present embodiment, by controlling the concentrations of each comonomer and radical having polymerization activity in the reaction system, methacrylic resin in which the amount of methanol-soluble content is 5 mass % or less relative to 100 mass % of the total amount of methanol-soluble content and methanol-insoluble content and the yellowness index (YI) measured using a 10 cm optical path length cell for a 20 w/v % chloroform solution of the methanol-insoluble content is 0 to 7 can be produced.

In the case of attempting to increase the conversion rate at the polymerization end in typical batch radical polymerization, the amount of the oligomer component increases in the final stage of the polymerization, which adversely affects molding processability. Moreover, in the case of copolymerizing the methacrylic acid ester monomer and the N-substituted maleimide monomer, typically the N-substituted maleimide monomer tends to remain, and a low molecular weight polymer with high N-substituted maleimide content forms in the final stage of the polymerization. The polymer itself exhibits colorability or, when heated, causes the formation of a polymer which is a coloring component.

In the polymerization of the methacrylic resin having the N-substituted maleimide monomer-derived ring structural unit in the present embodiment, the polymerization initiator and/or the monomer are added during the polymerization. By controlling their additive amounts, the variation of the concentration ratio between the monomer and the radical in the system in the polymerization is reduced, and the formation of a low molecular weight component in the final stage of the polymerization is suppressed, thus improving color tone and molding processability.

A first polymerization method is a method in which, in batch or semibatch polymerization, a radical polymerization initiator whose half-life at the polymerization temperature is 1 min or more and less than 60 min is used, and the radical polymerization initiator is added into the reactor while gradually decreasing the additive amount per unit time, thus promoting the monomer polymerization.

A second polymerization method is a method in which, in batch or semibatch polymerization, a radical polymerization initiator whose half-life at the polymerization temperature is 60 min or more is used, and a part of the radical polymerization initiator is added into the reactor within a predetermined time from the start of polymerization, and a part of the monomers is added after the predetermined time from the start of polymerization, thus promoting the polymerization.

Each polymerization method is described below.

As mentioned above, in the first polymerization method, a radical polymerization initiator whose half-life at the polymerization temperature is 1 min or more and less than 60 min is used, and the radical polymerization initiator is added into the reactor while gradually decreasing the additive amount per unit time, thus promoting the monomer polymerization.

Here, the radical polymerization initiator whose half-life at the polymerization temperature is 1 min or more and less than 60 min can be regarded as a radical polymerization initiator whose polymerization temperature is lower than or equal to the one-minute half-life temperature and higher than the one-hour half-life temperature.

An initiator whose half-life is 1 min or more at the polymerization temperature is preferable because the initiator added to the polymerization reactor is sufficiently mixed with the content fluid and then decomposed to start the polymerization. Moreover, by adding the initiator whose half-life is much shorter than the polymerization time in the polymerization, the variation of the ratio of the residual monomer concentration to the radical concentration in the reaction system can be kept low, and the radical concentration when the residual monomer concentration has decreased in the final stage of the polymerization can be kept low. Thus, the formation of a low molecular weight component in the polymerization can be suppressed.

The half-life of the radical polymerization initiator at the polymerization temperature is preferably 3 min or more and less than 60 min, and further preferably 5 min or more and less than 60 min.

The one-minute half-life temperature and the one-hour half-life temperature are described in documents, technical data of peroxide manufacturers, and so on. The half-life temperature in other times can also be calculated by further using data of decomposition reaction activation energy.

Examples of the half-life temperatures of several radical initiators are listed in Table 1.

TABLE 1

| | | Half-life temperature (° C.) | | | | | | |
|---|---|---|---|---|---|---|---|---|
| | Compound name | 1 min | 3 min | 5 min | 1 hr | 2 hr | 3 hr | 10 hr |
| Peroxy esters | 3-hydroxy-1,1-dimethylbutylperoxyneodecanoate | 91 | 80 | 76 | 54 | 49 | 46 | 37 |
| | α-cumylperoxyneodecanoate | 94 | 83 | 78 | 55 | 49 | 46 | 37 |
| | 1,1,3,3-tetramethylbutylperoxyneodecanoate | 92 | 82 | 78 | 58 | 52 | 49 | 41 |
| | 1,1,3,3-tetramethylbutylperoxy-2-ethylhexanoate | 124 | 113 | 108 | 84 | 78 | 75 | 65 |
| | t-butylperoxyneodecanoate | 104 | 92 | 87 | 65 | 59 | 56 | 46 |
| | t-butylperoxyneoheptanoate | 112 | 100 | 95 | 72 | 66 | 63 | 53 |
| | 1-butylperoxypivalate | 110 | 100 | 95 | 73 | 67 | 64 | 55 |
| | t-butylperoxy-2-ethylhexanoate | 134 | 122 | 116 | 92 | 86 | 82 | 72 |
| | t-butylperoxyisobutylate | 127 | 121 | 116 | 95 | 86 | 83 | 79 |
| | t-butylperoxyacetate | 160 | 149 | 144 | 121 | 115 | 112 | 102 |
| | t-butylperoxy-3,5,5-trimethylhexanoate | 166 | 152 | 146 | 119 | 112 | 108 | 97 |
| | t-butylperoxyisononanoate | 167 | 154 | 149 | 123 | 117 | 113 | 102 |
| | t-amylperoxyneodecanoate | 99 | 89 | 84 | 64 | 58 | 55 | 46 |
| | 1-amylperoxypivalate | 112 | 101 | 96 | 74 | 68 | 65 | 55 |
| | t-amylperoxy-2-ethylhexanoate | 125 | 112 | 108 | 88 | 83 | 80 | 70 |
| | t-amylperoxynormaloctoate | 157 | 145 | 140 | 116 | 110 | 106 | 96 |
| | t-amylperoxyacetate | 162 | 150 | 144 | 120 | 114 | 110 | 100 |
| | t-amylperoxyisononanoate | 152 | 141 | 136 | 114 | 109 | 105 | 96 |
| | t-amylperoxybenzoate | 166 | 153 | 147 | 122 | 115 | 111 | 100 |
| | t-butylperoxy-2-ethylhexylmonocarbonate | 161 | 149 | 144 | 119 | 113 | 109 | 99 |
| | t-hexylperoxyneodecanoate | 101 | 90 | 85 | 63 | 57 | 54 | 45 |

TABLE 1-continued

|  | Compound name | Half-life temperature (° C.) | | | | | | |
|---|---|---|---|---|---|---|---|---|
|  |  | 1 min | 3 min | 5 min | 1 hr | 2 hr | 3 hr | 10 hr |
|  | t-butylperoxyneoheptanoate | 105 | 94 | 89 | 68 | 63 | 60 | 51 |
|  | 1-hexylperoxypivalale | 109 | 98 | 93 | 71 | 66 | 62 | 53 |
|  | 2,5-dimethyl-2,5-di(2-ethylhexanoylperoxy)hexane | 119 | 109 | 104 | 83 | 78 | 75 | 66 |
|  | t-hexylperoxy-2-ethylhexanoate | 133 | 120 | 115 | 90 | 84 | 80 | 70 |
|  | t-hexylperoxyisopropylmonocarbonate | 155 | 143 | 138 | 115 | 108 | 105 | 95 |
|  | t-butylperoxymaleicacid | 168 | 153 | 147 | 119 | 112 | 108 | 96 |
|  | t-butylperoxylaurate | 159 | 148 | 142 | 118 | 112 | 108 | 98 |
|  | t-butylperoxyisopropylmonocarbonate | 159 | 147 | 142 | 118 | 112 | 109 | 99 |
|  | t-hexylperoxybenzoate | 160 | 148 | 143 | 119 | 113 | 110 | 99 |
|  | 2,5-dimethyl-2,5-di(benzoylperoxy)hexane | 158 | 147 | 142 | 119 | 113 | 109 | 100 |
|  | t-butylperoxybenzoate | 167 | 155 | 149 | 125 | 118 | 115 | 104 |
| Peroxy carbonates | t-butylperoxyisopropylcarbonate | 159 | 147 | 142 | 118 | 112 | 109 | 99 |
|  | t-butylperoxy-2-ethylhexylcarbonate | 166 | 153 | 147 | 121 | 115 | 111 | 100 |
|  | t-amylperoxyisopropylcarbonate | 153 | 142 | 137 | 115 | 109 | 106 | 96 |
|  | t-amylperoxy-2-ethylhexylcarbonate | 155 | 146 | 141 | 117 | 110 | 107 | 99 |
| Dialkyl peroxides | dicumylperoxide | 175 | 164 | 159 | 136 | 130 | 126 | 116 |
|  | 2,5-dimethyl-2,5-di(t-butylperoxy)hexane | 180 | 168 | 162 | 138 | 132 | 128 | 118 |
|  | di(24-butylperoxyisopropyhbenzene | 175 | 165 | 160 | 138 | 132 | 129 | 119 |
|  | di-t-butylperoxide | 186 | 174 | 169 | 144 | 138 | 134 | 124 |
|  | 2,5-dimethyl-2,5-di(t-butylperoxy)hexyne-3 | 194 | 182 | 176 | 150 | 143 | 139 | 128 |
|  | di-t-amylperoxide | 184 | 172 | 167 | 143 | 137 | 133 | 123 |
|  | t-butylcumylperoxide | 173 | 163 | 158 | 137 | 132 | 129 | 120 |
|  | di-t-hexylperoxide | 177 | 165 | 160 | 136 | 130 | 126 | 116 |
| Peroxy ketals | 1,1-di(t-butylperoxy)cyclohexane | 154 | 141 | 136 | 111 | 105 | 101 | 91 |
|  | 2,2-di-(t-butylperoxy)butane | 160 | 149 | 144 | 122 | 116 | 113 | 103 |
|  | n-butyl-4,4-di(t-butylperoxy)valerate | 173 | 159 | 153 | 127 | 120 | 116 | 105 |
|  | ethyl-3,3-di(t-butylperoxy)butyrate | 175 | 163 | 158 | 134 | 128 | 124 | 114 |
|  | 1,1-di(t-amylperoxy)cyclohexane | 150 | 139 | 134 | 112 | 106 | 103 | 93 |
|  | 1,1-di(t-butylperoxy)-2-methylcyclohexane | 142 | 131 | 126 | 102 | 96 | 93 | 83 |
|  | 1,1-di(t-hexylperoxy)-3,3,5-trimethylcyclohexane | 147 | 135 | 130 | 106 | 100 | 97 | 87 |
|  | 1,1-di(t-hexylperoxy)cyclohexane | 149 | 137 | 132 | 107 | 101 | 97 | 87 |
|  | 2,2-di(4,4-di-(t-butylperoxy)cyclohexyhpropane | 154 | 142 | 137 | 114 | 108 | 105 | 95 |
| Peroxy dicarbonates | di(2-ethylhexyhperoxydicarbonate | 91 | 82 | 78 | 59 | 54 | 52 | 44 |
|  | di-sec-butylperoxydicarbonate | 92 | 82 | 78 | 57 | 52 | 49 | 41 |
|  | di-n-propylperoxydicarbonate | 94 | 84 | 79 | 58 | 52 | 49 | 40 |
|  | diisopropylperoxydicarbonate | 88 | 79 | 75 | 56 | 51 | 49 | 41 |
|  | di(44-butylcyclohexyhperoxydicarbonate | 92 | 82 | 78 | 58 | 52 | 49 | 41 |
| Hydro peroxides | 1,1,3,3-tetramethylbutylhydroperoxide | 247 | 228 | 219 | 182 | 173 | 168 | 153 |
|  | t-butylhydroperoxide | 261 | 242 | 233 | 196 | 187 | 182 | 167 |
|  | t-amylhydroperoxide | 219 | 209 | 204 | 183 | 177 | 174 | 165 |
|  | cumenehydroperoxide | 254 | 235 | 226 | 188 | 179 | 173 | 158 |
|  | p-menthanehydroperoxide | 200 | 185 | 179 | 151 | 144 | 140 | 128 |
|  | diisopropylbenzenehydroperoxide | 233 | 215 | 207 | 173 | 164 | 159 | 145 |
| Diacyl peroxides | di(3,5,5-trimethylhexanoyl)peroxide | 113 | 102 | 98 | 77 | 71 | 68 | 59 |
|  | dilauroylperoxide | 116 | 106 | 101 | 80 | 74 | 71 | 62 |
|  | dibenzoylperoxide | 130 | 119 | 114 | 92 | 86 | 83 | 74 |
|  | diisobutylperoxide | 85 | 75 | 70 | 50 | 44 | 41 | 33 |
|  | disuccinicacidperoxide | 132 | 119 | 113 | 87 | 80 | 77 | 66 |
|  | di(4-methylbenzoyl)peroxide | 128 | 117 | 112 | 89 | 83 | 80 | 71 |

In the first polymerization method, the additive amount of the initiator added after the polymerization conversion rate reaches 85% is preferably 10 mass % to 25 mass % and more preferably 10 mass % to 20 mass %, relative to 100 mass % of the total additive amount of the radical polymerization initiator added in the polymerization period.

In the first polymerization method, when adding the radical polymerization initiator whose half-life at the polymerization temperature is 1 min or more and less than 60 min into the reactor while gradually decreasing the additive amount per unit time to promote the monomer polymerization, the addition rate of the initiator when the polymerization conversion rate reaches 85% is preferably 1/10 to 1/3 of the maximum addition rate, and more preferably 1/10 to 1/4 of the maximum addition rate.

The above-mentioned addition rate not less than the lower limit is preferable in terms of obtaining a sufficient conversion rate. The above-mentioned addition rate not more than the upper limit is preferable in terms of suppressing the formation of any polymer component adversely affecting color tone and processability.

In the first polymerization method, by feeding a part of the monomer into the reactor before the polymerization start and, after adding the polymerization initiator to start the polymerization, feeding the remaining part of the monomer, the formation of an ultrahigh molecular weight component is suppressed as well as the formation of a low molecular weight component. Hence, the molecular weight distribution can be narrowed to adjust Mw/Mn and Mz/Mw to the desired ranges. Furthermore, the residual N-substituted maleimide monomer content in the final stage of the polymerization can be reduced, which contributes to favorable color tone.

The ratio of the amount of the monomer fed initially and the amount of the monomer added after the polymerization start is preferably 1:9 to 8:2, more preferably 2:8 to 7.5:2.5, and further preferably 3:7 to 5:5.

In the first polymerization method, the additive amount of the methacrylic acid ester monomer which tends to polymerize first in copolymerization is decreased in initial feeding and increased in additional feeding. In this way, the residual amount of the N-substituted maleimide monomer in the final stage of the polymerization can be reduced, which is preferable in terms of color tone improvement.

Moreover, by adding a monomer such as styrene having high alternating copolymerizability with the N-substituted maleimide monomer during the polymerization, the residual amount of the N-substituted maleimide monomer can be reduced.

As mentioned above, in the second polymerization method, a radical polymerization initiator whose half-life at the polymerization temperature is 60 min or more is used, and a part of the radical polymerization initiator is added into the reactor within the predetermined time from the start of polymerization, and a part of the monomer is added into the reactor after the predetermined time from the start of polymerization, to promote the polymerization.

In the case of using a radical initiator whose half-life is not very short as compared with the polymerization time, the radical concentration is kept relatively high even in the final stage of the polymerization.

Here, by additionally feeding the monomer in the final stage of the polymerization, the variation of the ratio of the residual monomer concentration to the radical concentration in the polymerization period can be reduced. Moreover, by feeding a large amount of the radical initiator in the initial stage of the polymerization, the radical concentration when the residual monomer concentration has decreased in the final stage of the polymerization can be kept low, with it being possible to suppress the formation of a low molecular weight component in the polymerization.

In the second polymerization method, 25 mass % or more of the total additive amount of the radical initiator is added within 30 min from the addition start of the polymerization initiator. Preferably, 33 mass % or more of the total additive amount is added. Further preferably, 50 mass % or more of the total additive amount is added.

25 mass % or more of the total additive amount of the monomer is added after 30 min from the addition start of the polymerization initiator. Preferably, 33 mass % or more of the total additive amount is added. More preferably, 50 mass % or more of the total additive amount is added. Further preferably, 66 mass % or more of the total additive amount is added.

In the second polymerization method, the addition of the total additive amount of the radical initiator is completed preferably within 4 hours from the addition start of the polymerization initiator, more preferably within 3 hours from the addition start of the polymerization initiator, and further preferably within 2 hours from the addition start of the polymerization initiator.

In the first and second manufacturing methods of the methacrylic resin including the N-substituted maleimide-based structural unit (B-1) as the structural unit (B) having a cyclic structure-containing main chain, two or more types of radical initiators can be used in combination.

In the case where the half-life at the polymerization temperature is 1 min or more and less than 60 min in all of the two or more types of radical initiators and in the case where the half-life at the polymerization temperature is 60 min or more in all of the two or more types of radical initiators, the additive amount and addition rate of the radical initiator in the respective first and second polymerization methods may be the sum of the additive amounts and addition rates of the two or more types of radical initiators.

In the case of using a radical initiator whose half-life at the polymerization temperature is 1 min or more and less than 60 min and a radical initiator whose half-life at the polymerization temperature is 60 min or more in combination, the second polymerization method is employed. In detail, 25 mass % or more of the total additive amount of the radical polymerization initiator is added within 30 min from the addition start of the polymerization initiator, and 25 mass % or more of the total additive amount of the monomer is added after 30 min from the addition start of the polymerization initiator.

No specific limitations are placed on the method by which a polymerized product is collected from the polymerization solution obtained through solution polymerization. Examples of methods that can be adopted include a method in which the polymerization solution is added into an excess of a poor solvent in which the polymerized product obtained through polymerization does not dissolve, such as a hydrocarbon solvent or an alcohol solvent, treatment (emulsifying dispersion) is subsequently performed using a homogenizer, and unreacted monomers are separated from the polymerization solution by pre-treatment such as liquid-liquid extraction or solid-liquid extraction; and a method in which the polymerization solvent and unreacted monomers are separated by a step referred to as a devolatilization step to collect the polymerized product. The method preferably comprises the devolatilization step from a viewpoint of productivity.

The devolatilization step is a step in which volatile content such as the polymerization solvent, residual monomers, and reaction by-products are removed under heated vacuum conditions.

Examples of devices that can be used in the devolatilization step include devolatilization devices comprising a tubular heat exchanger and a devolatilization tank; thin film evaporators such as WIPRENE and EXEVA produced by Kobelco Eco-Solutions Co., Ltd., and Kontro and Diagonal-Blade Kontro produced by Hitachi, Ltd.; and vented extruders having sufficient residence time and surface area for displaying devolatilization capability.

Moreover, it is possible to adopt a devolatilization step or the like in which a devolatilization device that is a combination of two or more of these devices is used.

The treatment temperature in the devolatilization device is preferably 150° C. to 350° C., more preferably 170° C. to 300° C., and even more preferably 200° C. to 280° C. A temperature of not less than the lower limit can reduce residual volatile matter. A temperature of not more than the upper limit can suppress coloring or decomposition of the obtained acrylic resin.

The degree of vacuum in the devolatilization device may be in a range of 10 Torr to 500 Torr, and preferably in a range of 10 Torr to 300 Torr. A degree of vacuum of not more than the upper limit can reduce the residual amount of volatile matter. A degree of vacuum of not less than the lower limit is practical in industrial operation.

The treatment time is selected as appropriate depending on the amount of residual volatile matter. To suppress coloring or decomposition of the obtained acrylic resin, the treatment time is preferably as short as possible.

The polymerized product collected through the devolatilization step is pelletized through a step referred to as a pelletization step.

In the pelletization step, molten resin is extruded from a porous die as strands and is then pelletized by cold cutting, hot cutting in air, strand cutting in water, or under water cutting.

In a situation in which a vented extruder is used as a devolatilization device, the devolatilization step and the pelletization step may be combined.

The method of manufacturing the methacrylic resin including the lactone ring structural unit (B-2) as the structural unit (B) having a cyclic structure-containing main chain is described in detail below.

As the method of manufacturing the methacrylic resin having the lactone ring structural unit (B-2) in the main chain in the present embodiment, solution polymerization using a solvent is preferable in terms of facilitating cyclization reaction. Here, a method of forming the lactone ring structure by cyclization reaction after polymerization may be used.

Examples of the polymerization solvent used include aromatic hydrocarbons such as toluene, xylene, and ethylbenzene; and ketones such as methyl ethyl ketone and methyl isobutyl ketone.

One of these solvents may be used individually, or two or more of these solvents may be used together.

No specific limitations are placed on the amount of solvent used in polymerization so long as polymerization can proceed and gelation is inhibited. However, when the total amount of monomer that is used is taken to be 100 parts by mass, the amount of solvent is, for example, preferably 50 parts by mass to 200 parts by mass, and more preferably 100 parts by mass to 200 parts by mass.

In order to sufficiently inhibit gelation of the polymerization solution and promote the cyclization reaction after polymerization, polymerization is preferably performed such that the concentration of produced polymer in the reaction mixture obtained after polymerization is 50 mass % or less, and this concentration is preferably controlled to 50 mass % or less by adding polymerization solvent to the reaction mixture as appropriate.

The method by which the polymerization solvent is added to the reaction mixture as appropriate is not specifically limited and may, for example, be through continuous addition of the polymerization solvent or intermittent addition of the polymerization solvent.

The polymerization solvent that is added may be a single type of solvent, or may be a mixed solvent of two or more types of solvents.

Although no specific limitations are placed on the polymerization temperature other than being a temperature at which polymerization proceeds, the polymerization temperature is preferably 50° C. to 200° C., and more preferably 80° C. to 180° C. from a viewpoint of productivity.

Although no specific limitations are placed on the polymerization time so long as the target conversion rate can be achieved, the polymerization time is preferably 0.5 hours to 10 hours, and more preferably 1 hour to 8 hours from a viewpoint of productivity and so forth.

The polymerization conversion rate at the polymerization end of the methacrylic resin having the lactone ring structural unit in the main chain in the present embodiment may be a polymerization conversion rate disclosed in relation to the above-mentioned method of preparing the methacryl resin having the N-substituted maleimide monomer-derived structural unit.

In polymerization reaction, a chain transfer agent may be added according to need.

The chain transfer agent may be a chain transfer agent typically used in radical polymerization. For example, a chain transfer agent disclosed in relation to the above-mentioned preparation method for the methacryl resin having the N-substituted maleimide monomer-derived structural unit may be used.

These may be used singly or in combination of two or more types.

The chain transfer agent may be added at any stage while polymerization reaction is in progress, and so the addition timing is not limited.

The additive amount of the chain transfer agent is not limited as long as a desired polymerization degree is achieved in the polymerization condition under which the chain transfer agent is used. The additive amount of the chain transfer agent may be 0.01 parts to 1 parts by mass and preferably 0.05 parts to 0.5 parts by mass, relative to 100 parts by mass of the total amount of the monomers used in polymerization.

The dissolved oxygen concentration in the polymerization solution may be, for example, a value disclosed in relation to the above-mentioned method of preparing the methacryl resin having the N-substituted maleimide monomer-derived structural unit.

In polymerization reaction, a polymerization initiator is added.

The polymerization initiator may be, but is not specifically limited to, any of the polymerization initiators disclosed in relation to the production method of the methacrylic resin including the N-substituted maleimide monomer-derived structural unit.

One of these polymerization initiators may be used individually, or two or more of these polymerization initiators may be used together.

The additive amount of the polymerization initiator is not limited, and may be set as appropriate depending on the monomer combination, the reaction condition, and the like. The additive amount of the polymerization initiator may be 0.01 parts to 1 parts by mass and preferably 0.05 parts to 0.5 parts by mass, relative to 100 parts by mass of the total amount of the monomers used in polymerization.

In the polymerization of the methacrylic resin having the lactone ring structural unit in the present embodiment, the polymerization initiator and, according to need, the monomer are added during the polymerization. By controlling their additive amounts, the variation of the concentration ratio between the monomer and the radical in the system during the polymerization is reduced, and the formation of a low molecular weight component in the final stage of the polymerization is suppressed, thus improving color tone and molding processability.

A first polymerization method is a method in which, in batch or semibatch polymerization, a radical polymerization initiator whose half-life at the polymerization temperature is 1 min or more and less than 60 min is used, and the radical polymerization initiator is added into the reactor while gradually decreasing the additive amount per unit time, thus promoting the monomer polymerization.

A second polymerization method is a method in which, in batch or semibatch polymerization, a radical polymerization initiator whose half-life at the polymerization temperature is 60 min or more is used, and a part of the radical polymerization initiator is added into the reactor within a predetermined time from the start of polymerization, and a part of the monomers is added after the predetermined time from the start of polymerization, thus promoting the polymerization.

Each polymerization method is described below.

As mentioned above, in the first polymerization method, a radical polymerization initiator whose half-life at the polymerization temperature is 1 min or more and less than 60 min is used, and the radical polymerization initiator is added into the reactor while gradually decreasing the additive amount per unit time, thus promoting the monomer polymerization.

Here, the radical polymerization initiator whose half-life at the polymerization temperature is 1 min or more and less than 60 min can be rephrased as a radical polymerization initiator whose polymerization temperature is lower than or equal to the one-minute half-life temperature and higher than the one-hour half-life temperature.

An initiator whose half-life is 1 min or more at the polymerization temperature is preferable because the initiator added to the polymerization reactor is sufficiently mixed with the content fluid and then decomposed to start the polymerization. Moreover, by adding the initiator whose half-life is much shorter than the polymerization time in the polymerization, the variation of the residual monomer concentration to the radical concentration in the reaction system can be kept low, and the radical concentration when the residual monomer concentration has decreased in the final stage of the polymerization can be kept low. Thus, the formation of a low molecular weight component in the polymerization can be suppressed.

The half-life of the radical polymerization initiator at the polymerization temperature is preferably 3 min or more and less than 60 min, and further preferably 5 min or more and less than 60 min.

The meaning and calculation method of the half-life temperature and an example of the half-life temperature of the radical initiator are as disclosed in relation to the above-mentioned preparation method for the methacryl resin having the N-substituted maleimide monomer-derived structural unit.

In the first polymerization method, the additive amount of the initiator added after the polymerization conversion rate reaches 85% is preferably 10 mass % to 25 mass % and more preferably 10 mass % to 20 mass %, relative to 100 mass % of the total additive amount of the radical polymerization initiator added in the polymerization period.

In the first polymerization method, when adding the radical polymerization initiator whose half-life at the polymerization temperature is 1 min or more and less than 60 min into the reactor while gradually decreasing the additive amount per unit time to promote the monomer polymerization, the addition rate of the initiator when the polymerization conversion rate reaches 85% is preferably 1/10 to 1/3 of the maximum addition rate, and more preferably 1/10 to 1/4 of the maximum addition rate.

The above-mentioned addition rate not less than the lower limit is preferable in terms of obtaining a sufficient conversion rate. The above-mentioned addition rate not more than the upper limit is preferable in terms of suppressing the formation of any polymer component adversely affecting color tone and processability.

In the first polymerization method, by feeding a part of the monomer into the reactor before the polymerization start and, after adding the polymerization initiator to start the polymerization, feeding the remaining part of the monomer, the formation of an ultrahigh molecular weight component is suppressed as well as the formation of a low molecular weight component. Hence, the molecular weight distribution can be narrowed to adjust Mw/Mn and Mz/Mw to the desired ranges. Furthermore, by introducing the acrylate monomer having the hydroxy group uniformly into the molecules as discontinuously as possible, the intramolecular cyclization rate can be increased to suppress gelation and further suppress color tone degradation. In view of this, it is preferable to add the monomer after the polymerization start.

The ratio of the amount of the monomer fed initially and the amount of the monomer added after the polymerization start is preferably 1:9 to 8:2, more preferably 2:8 to 7.5:2.5, and further preferably 3:7 to 5:5.

As mentioned above, in the second polymerization method, a radical polymerization initiator whose half-life at the polymerization temperature is 60 min or more is used, and a part of the radical polymerization initiator is added into the reactor within the predetermined time from the start of polymerization, and a part of the monomer is added into the reactor after the predetermined time from the start of polymerization, to promote the polymerization.

In the case of using a radical initiator whose half-life is not very short as compared with the polymerization time, the radical concentration is kept relatively high even in the final stage of the polymerization.

Here, by additionally feeding the monomer in the final stage of the polymerization, the variation of the ratio of the residual monomer concentration to the radical concentration in the polymerization period can be reduced. Moreover, by feeding a large amount of the radical initiator in the initial stage of the polymerization, the radical concentration when the residual monomer concentration has decreased in the final stage of the polymerization can be kept low, with it being possible to suppress the formation of a low molecular weight component in the polymerization.

In the second polymerization method, 25 mass % or more of the total additive amount of the radical initiator is added within 30 min from the addition start of the polymerization initiator. Preferably, 33 mass % or more of the total additive amount is added. Further preferably, 50 mass % or more of the total additive amount is added.

25 mass % or more of the total additive amount of the monomer is added after 30 min from the addition start of the polymerization initiator. Preferably, 33 mass % or more of the total additive amount is added. More preferably, 50 mass % or more of the total additive amount is added. Further preferably, 66 mass % or more of the total additive amount is added.

In the second polymerization method, the addition of the total additive amount of the radical initiator is completed preferably within 4 hours from the addition start of the polymerization initiator, more preferably within 3 hours from the addition start of the polymerization initiator, and further preferably within 2 hours from the addition start of the polymerization initiator.

In the first and second manufacturing methods of the methacrylic resin including the lactone ring structural unit (B-2) as the structural unit (B) having a cyclic structure-containing main chain, two or more types of radical initiators can be used in combination.

In the case where the half-life at the polymerization temperature is 1 min or more and less than 60 min in all of the two or more types of radical initiators and in the case where the half-life at the polymerization temperature is 60 min or more in all of the two or more types of radical initiators, the additive amount and addition rate of the radical initiator in the respective first and second polymerization methods may be the sum of the additive amounts and addition rates of the two or more types of radical initiators.

In the case of using a radical initiator whose half-life at the polymerization temperature is 1 min or more and less than 60 min and a radical initiator whose half-life at the polymerization temperature is 60 min or more in combination, the second polymerization method is employed. In detail, 25 mass % or more of the total additive amount of the radical polymerization initiator is added within 30 min from the addition start of the polymerization initiator, and 25 mass % or more of the total additive amount of the monomer is added after 30 min from the addition start of the polymerization initiator.

The methacrylic resin according to the present embodiment that includes the lactone ring structural unit can be obtained by performing a cyclization reaction after completion of the polymerization reaction. Therefore, the polymerization reaction liquid is preferably subjected to the lactone cyclization reaction in a solvent-containing state without removing the polymerization solvent therefrom.

The copolymer obtained through polymerization is heat treated to cause a cyclocondensation reaction between a hydroxy group and an ester group present in the molecular chain of the copolymer and thereby form a lactone ring structure.

Heat treatment for formation of the lactone ring structure may be performed, for example, using a reaction apparatus including a vacuum device or devolatilization device for removal of alcohol that may be produced as a by-product of cyclocondensation, or an extruder including a devolatilization device.

In formation of the lactone ring structure, the heat treatment may be performed in the presence of a cyclocondensation catalyst to promote the cyclocondensation reaction.

Specific examples of cyclocondensation catalysts that can be used include monoalkyl, dialkyl, and trialkyl esters of phosphorus acid such as methyl phosphite, ethyl phosphite, phenyl phosphite, dimethyl phosphite, diethyl phosphite, diphenyl phosphite, trimethyl phosphite, and triethyl phosphite; and monoalkyl, dialkyl, and trialkyl esters of phosphoric acid such as methyl phosphate, ethyl phosphate, 2-ethylhexyl phosphate, octyl phosphate, isodecyl phosphate, lauryl phosphate, stearyl phosphate, isostearyl phosphate, dimethyl phosphate, diethyl phosphate, di-2-ethylhexyl phosphate, diisodecyl phosphate, dilauryl phosphate, distearyl phosphate, diisostearyl phosphate, trimethyl phosphate, triethyl phosphate, triisodecyl phosphate, trilauryl phosphate, tristearyl phosphate, and triisostearyl phosphate.

One of these cyclocondensation catalysts may be used individually, or two or more of these cyclocondensation catalysts may be used together.

Although the amount of cyclocondensation catalyst that is used is not specifically limited, the amount of the cyclocondensation catalyst relative to 100 parts by mass of the methacrylic resin is, for example, preferably 0.01 parts by mass to 3 parts by mass, and more preferably 0.05 parts by mass to 1 part by mass.

If the usage of the catalyst is less than 0.01 parts by mass, there is a possibility that the cyclization condensation reaction rate is not sufficiently improved. If the usage of the catalyst is more than 3 parts by mass, there is a possibility that coloring of the obtained polymer and crosslinking of the polymer, which hampers melt molding, occurs.

The timing of addition of the cyclocondensation catalyst is not specifically limited. For example, the cyclocondensation catalyst may be added in an initial stage of the cyclocondensation reaction, may be added partway through the reaction, or may be added both in the initial stage and partway through the reaction.

In a situation in which the cyclocondensation reaction is carried out in the presence of a solvent, devolatilization is preferably carried out concurrently with the reaction.

Although no specific limitations are placed on the device used in a situation in which the cyclocondensation reaction and a devolatilization step are carried out concurrently, it is preferable to use a devolatilization device comprising a heat exchanger and a devolatilization tank, a vented extruder, or an apparatus in which a devolatilization device and an extruder are arranged in series, and more preferable to use a vented twin-screw extruder.

The vented twin-screw extruder is preferably a vented extruder equipped with a plurality of vent ports.

In a situation in which a vented extruder is used, the reaction treatment temperature is preferably 150° C. to 350° C., and more preferably 200° C. to 300° C. If the reaction treatment temperature is less than 150° C., there is a possibility that an increase in residual volatile matter is caused by insufficient cyclization condensation reaction. If the reaction treatment temperature is more than 350° C., there is a possibility that coloring or decomposition of the obtained polymer occurs.

Moreover, in a situation in which a vented extruder is used, the degree of vacuum therein is preferably 10 Torr to 500 Torr, and more preferably 10 Torr to 300 Torr. If the degree of vacuum is more than 500 Torr, volatile matter tends to remain. If the degree of vacuum is less than 10 Torr, industrial operation tends to be difficult.

When a cyclocondensation reaction is performed as described above, an alkaline earth metal and/or amphoteric metal salt of an organic acid is preferably added in pelletization to deactivate residual cyclocondensation catalyst.

Examples of the alkaline earth metal and/or amphoteric metal salt of an organic acid include calcium acetyl acetate, calcium stearate, zinc acetate, zinc octanoate, and zinc 2-ethylhexanoate.

After the cyclocondensation reaction step is completed, the methacrylic resin is melted and extruded as strands from an extruder equipped with a porous die, and is then pelletized by cold cutting, hot cutting in air, strand cutting in water, or under water cutting.

Lactonization for forming the lactone ring structural unit may be performed after resin production and before resin composition production (described later), or performed during resin composition production together with melt kneading of the resin and the components other than the resin.

A methacrylic resin according to the present embodiment preferably includes at least one cyclic structural unit selected from the group consisting of an N-substituted maleimide monomer-derived structural unit and a lactone ring structural unit. Of such cyclic structural units, it is particularly preferable that the methacrylic resin includes an N-substituted maleimide monomer-derived structural unit in terms that a high degree of control of optical properties such as the photoelastic coefficient can be easily achieved without blending with another thermoplastic resin.

—Other Thermoplastic Resins—

Another thermoplastic resin may be compounded in the methacrylic resin according to the present embodiment with the aim of adjusting birefringence or improving flexibility, so long as the objectives of the present embodiment are not impeded.

Examples of other thermoplastic resins that can be used include polyacrylates such as polybutyl acrylate; styrene polymers (for example, polystyrene, styrene-methyl methacrylate copolymer, styrene-butyl acrylate copolymer, styrene-acrylonitrile copolymer, and acrylonitrile-butadiene-styrene block copolymer); acrylic rubber particles having a 3 or 4 layer structure described in JP S59-202213 A, JP S63-27516 A, JP S51-129449 A, and JP S52-56150 A; rubbery polymers disclosed in JP S60-17406 B and JP H8-245854 A; and methacrylic rubber-containing graft copolymer particles obtained by multi-step polymerization described in WO 2014-002491 A1.

Of these other thermoplastic resins, from a viewpoint of obtaining good optical properties and mechanical properties, it is preferable to use a styrene-acrylonitrile copolymer or rubber-containing graft copolymer particles having a grafted portion in a surface layer thereof with a chemical composition that is compatible with the methacrylic resin including the structural unit (X) having a cyclic structure-containing main chain.

The average particle diameter of acrylic rubber particles, methacrylic rubber-containing graft copolymer particles, or a rubbery polymer such as described above is preferably 0.03 μm to 1 μm, and more preferably 0.05 μm to 0.5 μm from a viewpoint of improving impact strength, optical properties, and so forth of a film obtained using the composition according to the present embodiment.

The content of other thermoplastic resins relative to 100 parts by mass of the methacrylic resin is preferably 0 parts by mass to 50 parts by mass, and more preferably 0 parts by mass to 25 parts by mass.

—Additives—

The methacrylic resin in the present embodiment may contain various additives within the range of not significantly undermining the advantageous effects according to this disclosure.

The additives are not limited. Examples include inorganic fillers; pigments such as iron oxide; softeners/plasticizers such as stearic acid, behenic acid, zinc stearate, calcium stearate, magnesium stearate, and ethylenebisstearoamide; softeners/plasticizers such as paraffin-based process oil, naphthene-based process oil, aromatic-based process oil, paraffin, organic polysiloxane, and mineral oil; antioxidants such as hindered phenol-based antioxidant and sulfur-based antioxidant; hindered amine-based light stabilizers; benzotriazole-based ultraviolet absorbers; flame retardants; antistatic agents; reinforcing agents such as organic fiber, glass fiber, carbon fiber, and metal whisker; coloring agents; organic phosphorous compounds such as phosphite esters, phosphonites, and phosphate esters; other additives; and mixtures thereof.

EXAMPLE

The following provides a more specific description of the disclosed matter through examples and comparative examples. However, this disclosure is not limited to the following examples.

<1. Measurement of Polymerization Conversion Rate>

Part of a polymerization solution in each of the examples and comparative examples was collected. The sample was dissolved in chloroform, a 5 mass % solution was adjusted, and n-decane was added as an internal standard substance. The residual monomer concentration in the polymerization solution sample was measured using gas chromatography (GC-2010 made by Shimadzu Corporation), and the total mass (a) of the residual monomer in the polymerization solution was calculated. The polymerization conversion rate (%) was calculated from the total mass (a), the total mass (b) in the case of assuming that the total amount of the monomer added up to the collection of the sample remained in the polymerization solution, and the total mass (c) of the monomer added until the end of the polymerization step, according to calculation formula (b−a)/c×100.

<2. Analysis of Structural Units>

Unless otherwise noted in each of the production examples described below, the structural unit of the methacrylic resin produced in the production example was identified and its existence amount was calculated by $^1$H-NMR measurement and $^{13}$C-NMR measurement. The $^1$H-NMR and $^{13}$C-NMR measurement conditions were as follows.

Measurement device: DPX-400 made by Bruker Corporation.

Measurement solvent: $CDCl_3$ or DMSO-$d_6$.

Measurement temperature: 40° C.

In the case of a methacrylic resin having a lactone ring structure as the cyclic structure thereof, this structure was confirmed by a method described in JP 2001-151814 A or JP 2007-297620 A.

<3. Measurement of Molecular Weight and Molecular Weight Distribution>

The Z-average molecular weight (Mz), weight-average molecular weight (Mw), and number-average molecular weight (Mn) of the methacrylic resin produced in each of the below-mentioned production examples were measured by the following device and conditions:

Measurement device: Gel permeation chromatograph (HLC-8320GPC) produced by Tosoh Corporation Measurement conditions:

Column: TSK guard column Super H-H×1, TSK gel Super HM-M×2, TSK gel Super H2500×1; connected in series in this order Column temperature: 40° C.

Developing solvent: Tetrahydrofuran, 0.6 mL/min flow rate, 0.1 g/L of 2,6-di-t-butyl-4-methylphenol (BHT) added as internal standard Detector: Refractive index (RI) detector Detection sensitivity: 3.0 mV/min Sample: Solution of 0.02 g of methacrylic resin or methacrylic resin composition in 20 mL of tetrahydrofuran Injection amount: 10 μL Standard samples for calibration curve: Following 10 types of polymethyl methacrylate (PMMA Calibration Kit M-M-10 produced by Polymer Laboratories Ltd.) of differing molecular weight each having a known monodisperse weight peak molecular weight Weight peak molecular weight (Mp)
Standard sample 1: 1,916,000
Standard sample 2: 625,500
Standard sample 3: 298,900
Standard sample 4: 138,600
Standard sample 5: 60,150
Standard sample 6: 27,600
Standard sample 7: 10,290
Standard sample 8: 5,000
Standard sample 9: 2,810
Standard sample 10: 850

The RI detection intensity was measured with respect to the elution time of the methacrylic resin under the conditions set forth above.

The Z-average molecular weight (Mz), weight-average molecular weight (Mw), and number-average molecular weight (Mn) of the methacrylic resin were calculated based on a calibration curve obtained as a result of the measurement of the standard sample for calibration curve.

<4. Glass Transition Temperature>

The glass transition temperature (Tg) (° C.) of the methacrylic resin was measured according to JIS-K7121.

First, from each sample subjected to state adjustment (left for one week at 23° C.) in a standard state (23° C., 65% RH), test pieces at four points (four locations) of about 10 mg each were cut out.

Next, using a differential scanning calorimetry (Diamond DSC made by PerkinElmer Japan Co., Ltd.) under conditions of a nitrogen gas flow rate of 25 mL/min, the temperature was increased from room temperature (23° C.) to 200° C. at 10° C./min (primary temperature rise), and maintained at 200° C. for 5 min to completely melt the sample. After this, the temperature was decreased from 200° C. to 40° C. at 10° C./min, maintained at 40° C. for 5 min, and then increased again under the above-mentioned temperature rise conditions (secondary temperature rise). In the DSC curve drawn during this, the intersection point (intermediate-point glass transition temperature) between the stepped change portion curve during the secondary temperature rise and the straight line at equal distance in the vertical axis direction from each baseline extension was measured as the glass transition temperature (Tg) (° C.). Four points were subjected to measurement per sample, and the arithmetic mean of the four points (rounded off to the closest whole number) was set as the measurement value.

<5. Measurement of Photoelastic Coefficient $C_R$>

The methacrylic resin obtained in each of the examples and comparative examples was made into a press film using a vacuum compression molding machine, to obtain a measurement sample.

The specific sample preparation conditions were as follows. Using a vacuum compression molding machine (SFV-30 type made by SHINTO Metal Industries Corporation), the resin was preheated at 260° C. under reduced pressure (about 10 kPa) for 10 min. After this, the resin was compressed at 260° C. and about 10 MPa for 5 min. After the reduced pressure and the press pressure were released. The resin was then transferred to a cooling compression molding machine, and cooled and solidified. The obtained press film was cured for 24 hours or more in a constant temperature and humidity chamber adjusted to 23° C. and a humidity of 60%, and then a measurement test piece (thickness: about 150 μm, width: 6 mm) was cut out.

The photoelastic coefficient $C_R$ ($Pa^{-1}$) was measured using a birefringence measurement device described in detail in Polymer Engineering and Science 1999, 39, 2349-2357.

The film-like test piece was placed in a film tension device (made by Imoto Machinery Co., Ltd.) similarly installed in the constant temperature and humidity chamber, with a chuck interval of 50 mm. Next, a birefringence measurement device (RETS-100 made by Otsuka Electronics Co., Ltd.) was arranged so that its laser light path was situated in the center part of the film, and the birefringence of the test piece was measured while applying stretching stress at a strain rate of 50%/min (chuck interval: 50 mm, chuck moving speed: 5 mm/min).

From the relationship between the birefringence absolute value ($|\Delta n|$) obtained by the measurement and the stretching stress ($\sigma_R$), the slope of the straight line was determined by least squares approximation, and the photoelastic coefficient ($C_R$) ($Pa^{-1}$) was calculated. Data corresponding to a stretching stress of 2.5 MPa≤$\sigma_R$≤10 MPa was used for the calculation.

$$C_R = |\Delta n|/\sigma_R$$

where the birefringence absolute value ($|\Delta n|$) is defined as $$|\Delta n| = |nx - ny|$$

(nx: the refractive index in the stretching direction, ny: refractive index in the direction perpendicular to the stretching direction in plane).

<6. Measurement of Amount of Methanol-Soluble Content and Amount of Methanol-Insoluble Content>

With respect to each methacrylic resin obtained in the examples and comparative examples, 5 g of the methacrylic resin was dissolved in 100 mL of chloroform. The resultant solution was added into a dropping funnel and was then dripped into approximately 1 L of methanol stirred by a stirrer over 1 hour to cause re-precipitation. After the entire solution had been dripped into the methanol and then been left for 1 hour at rest, vacuum filtration was performed using a membrane filter (T05A090C produced by Advantec Mfs. Inc.) as a filter.

The filtration residue was vacuum dried for 16 hours at 60° C. and the dried product was taken to be methanol-insoluble content. Additionally, solvent was removed from the filtrate using a rotary evaporator with a bath temperature of 40° C. and a degree of vacuum that was gradually reduced from an initial setting of 390 Torr to a final level of 30 Torr. Soluble content remaining in the rotary evaporator flask was collected and taken to be methanol-soluble content.

The mass of the methanol-insoluble content and the mass of the methanol-soluble content were weighed and then the ratio (mass %) (methanol-soluble content ratio) of the amount of the methanol-soluble content to the total amount of the methanol-soluble content and the methanol-insoluble content (100 mass %) was calculated.

<7. Measurement of Yellowness Index (YI) and 680 nm Transmittance>

The methanol-insoluble content of the methacrylic resin obtained in each of the examples and comparative examples was made into a 20 w/v % chloroform solution (i.e. a solution produced by dissolving 10 g of the sample in chloroform to obtain a 50 mL solution), as a measurement sample. Transmittance measurement was conducted using an ultraviolet and visible spectrophotometer (UV-2500PC made by Shimadzu Corporation), with a measurement wavelength of 380 nm to 780 nm, a slit width of 2 nm, a 10 cm optical path length cell of a viewing angle of 10°, use of an supplementary illuminant C, and chloroform as a reference object.

YI (yellowness index) was calculated according to JIS K 7373 using an XYZ color system, based on the following formula:

$$YI = 100(1.2769X - 1.0592Z)/Y.$$

The transmittance (%) in a wavelength of 680 nm was also recorded under the same conditions as in the YI measurement.

<8. Film Formation Evaluation of Methacrylic Resin>

The methacrylic resin obtained in each of the below-mentioned examples and comparative examples was dried at 90° C. for 24 hours by dehumidified air, to reduce the water content to 300 mass ppm or less. After this, film formation was performed by the following method.

A film was prepared using a 15 mmφ twin screw extruder (made by TECHNOVEL Corporation) with a T die of 300 mm in width installed at its extruder tip portion. The film formation conditions were as follows: extruder tip portion set temperature: 260° C., T die temperature setting: 255° C., discharge rate: 1 kg/hr, and cooling roll set temperature: glass transition temperature −10° C. A film with a film thickness of 80 μm was thus obtained. After continuous operation for 6 hours under these conditions, an evaluation film of 1 m in length was collected.

A roll sufficiently cleaned before the start of film formation was used, and stains on the roll surface after 6 hours were visually observed. Each sample with the roll surface being roughly unchanged from that before the film formation and only a small part being slightly stained was evaluated as "excellent", each sample with the whole roll surface being slightly stained was evaluated as "good", each sample with the whole roll surface being stained and required for recleaning was evaluated as "poor".

[Raw Materials]

Raw materials used in the following examples and comparative examples were as shown below.

[[Monomers]]

Methyl methacrylate: produced by Asahi Kasei Chemicals Corporation

N-phenylmaleimide (phMI): produced by Nippon Shokubai Co., Ltd.

N-cyclohexylmaleimide (chMI): produced by Nippon Shokubai Co., Ltd.

Styrene: produced by Asahi Kasei Chemicals Corporation 2-(hydroxymethyl)methyl acrylate (MHMA): produced by Combi Bloks

[[Polymerization Initiators]]

1,1-di(t-butylperoxy)cyclohexane: "Perhexa C" produced by NOF Corporation 1,1-di(t-hexylperoxy)cyclohexane: "Perhexa HC" produced by NOF Corporation t-butylperoxyisopropylmonocarbonate: "Perbutyl I" produced by NOF Corporation t-amyl peroxyisononanoate: "Luperox 570" produced by ARKEMA Yoshitomi, Ltd.

t-butylperoxy-2-ethylhexanoate: "Perbutyl O" produced by NOF Corporation

[[Chain Transfer Agents]]

n-octylmercaptan: produced by Kao Corporation n-dodecylmercaptan: produced by Kao Corporation

[Example 1] Production of Methacrylic Resin (A) Having N-Substituted Maleimide Structural Unit A mixed monomer solution was prepared by measuring out 146.0 kg of methyl methacrylate (hereafter referred to as "MMA"), 14.6 kg of N-phenylmaleimide (hereafter referred to as "phMI"), 22.0 kg of N-cyclohexylmaleimide (hereafter referred to as "chMI"), 0.174 kg of n-octylmercaptan as a chain transfer agent, and 147.0 kg of m-xylene (hereafter referred to as "mXy"), adding these materials into a 1.25 m³ reactor equipped with a stirring blade and a temperature controller functioning through use of a jacket, and then stirring these materials.

Next, an additional mixed monomer solution was prepared by measuring out 271.2 kg of MMA, 27.1 kg of phMI, 40.9 kg of chMI, and 273.0 kg of mXy, adding these materials into a tank 1, and then stirring these materials.

Further, 58.0 kg of MMA was measured out in a tank 2.

For the content fluid in the reactor, nitrogen bubbling was performed at a rate of 30 L/min for 1 hours. For each of the tanks 1 and 2, nitrogen bubbling was performed at a rate of 10 L/min for 30 min. Dissolved oxygen was thus removed.

After this, steam was blown into the jacket to increase the solution temperature in the reactor to 124° C. While stirring at 50 rpm, a polymerization initiator solution obtained by dissolving 0.348 kg of 1,1-di(t-butylperoxy)cyclohexane in 4.652 kg of mXy was added at a rate of 2 kg/hr, thus starting polymerization.

During the polymerization, the solution temperature in the reactor was controlled to 124±2° C. through temperature adjustment using the jacket. After 30 min from the start of polymerization, the addition rate of the initiator solution was decreased to 1 kg/hr. Further, the additional mixed monomer solution was added from the tank 1 at 306.1 kg/hr for 2 hours.

Subsequently, after 2 hours and 45 min from the start of polymerization, the total amount of MMA was added from the tank 2 at a rate of 116 kg/hr for 30 min.

The addition rate of the initiator solution was further decreased to 0.5 kg/hr after 3.5 hours from the start of polymerization, to 0.25 kg/hr after 4.5 hours from the start of polymerization, and to 0.125 kg/hr after 6 hours from the start of polymerization. The addition was stopped after 7 hours from the start of polymerization.

After 10 hours from the start of polymerization, a polymerization solution including methacrylic resin having a cyclic structure-containing main chain was obtained.

The one-hour half-life temperature of 1,1-di(t-butylperoxy)cyclohexane used as the initiator was 111° C., the one-minute half-life temperature was 154° C., and the half-life at the polymerization temperature of 124° C. was 16 min.

After each of 4 hours, 6 hours, 8 hours, and 10 hours (polymerization end) from the start of polymerization, the polymer solution was sampled, and the polymerization conversion rate was analyzed from the residual monomer concentration. The results were 84.8% after 4 hours, 93.3% after 6 hours, 95.7% after 8 hours, and 96.0% after 10 hours.

This polymerization solution was fed into a concentrating device comprising a tubular heat exchanger and a vaporization tank that had been pre-heated to 170° C., to increase the concentration of the polymer in the solution to 70 mass %.

The resultant polymerization solution was fed into a thin-film evaporator having a heat transfer area of 0.2 m² and was subjected to devolatilization. The conditions used here were as follows: in-device temperature: 280° C., feed rate: 30 L/hr, rotational speed: 400 rpm, and degree of vacuum: 30 Torr. The polymerized product subjected to devolatilization was then pressurized using a gear pump, extruded from a strand die, cooled by water, and subsequently pelletized to obtain the methacrylic resin (A) having the N-substituted maleimide structural unit.

As a result of checking the composition of the resultant pellet polymer, the respective structural units derived from MMA, phMI, and chMI monomers were 81.3 mass %, 7.9 mass %, and 10.8 mass %. The weight-average molecular weight was 141,000, Mz/Mw was 1.54, and Mw/Mn was 1.94. The other physical properties are listed in Table 2.

[Example 2] Production of Methacrylic Resin (B) Having N-Substituted Maleimide Structural Unit A mixed monomer solution was prepared by measuring out 176.2 kg of MMA, 6.0 kg of phMI, 10.3 kg of chMI, 0.168 kg of n-octylmercaptan as a chain transfer agent, and 153.7 kg of mXy, adding these materials into a 1.25 m³ reactor equipped with a stirring blade and a temperature controller functioning through use of a jacket, and then stirring these materials.

Next, an additional mixed monomer solution was prepared by measuring out 327.1 kg of MMA, 11.2 kg of phMI, 19.2 kg of chMI, and 285.3 kg of mXy, adding these materials into a tank 1, and then stirring these materials.

Further, 11.0 kg of styrene was measured out in a tank 2.

For the content fluid in the reactor, nitrogen bubbling was performed at a rate of 30 L/min for 1 hour. For each of the tanks 1 and 2, nitrogen bubbling was performed at a rate of 10 L/min for 30 min. Dissolved oxygen was thus removed.

After this, steam was blown into the jacket to increase the solution temperature in the reactor to 124° C. While stirring at 50 rpm, a polymerization initiator solution obtained by dissolving 0.337 kg of 1,1-di(t-hexylperoxy)cyclohexane in 4.663 kg of mXy was added at a rate of 2 kg/hr, thus starting polymerization.

During the polymerization, the solution temperature in the reactor was controlled to 124±2° C. through temperature adjustment using the jacket. After 30 min from the start of polymerization, the addition rate of the initiator solution was decreased to 1 kg/hr. Further, the additional mixed monomer solution was added from the tank 1 at 257.1 kg/hr for 2.5 hours.

Subsequently, after 3 hours and 30 min from the start of polymerization, the total amount of styrene was added from the tank 2 at a rate of 44 kg/hr for 15 min.

The addition rate of the initiator solution was further decreased to 0.5 kg/hr after 3.5 hours from the start of polymerization, to 0.25 kg/hr after 4.5 hours from the start of polymerization, and to 0.125 kg/hr after 6 hours from the start of polymerization. The addition was stopped after 7 hours from the start of polymerization.

After 10 hours from the start of polymerization, a polymerization solution including methacrylic resin having a cyclic structure-containing main chain was obtained.

The one-hour half-life temperature of 1-di(t-hexylperoxy) cyclohexane used as the initiator was 107° C., the one-minute half-life temperature was 149° C., and the half-life at the polymerization temperature of 124° C. was 11 min.

After each of 4 hours, 6 hours, 8 hours, and 10 hours (polymerization end) from the start of polymerization, the polymer solution was sampled, and the polymerization conversion rate was analyzed from the residual monomer concentration. The results were 84.5% after 4 hours, 92.2% after 6 hours, 95.2% after 8 hours, and 95.5% after 10 hours.

This polymerization solution was fed into a concentrating device comprising a tubular heat exchanger and a vaporization tank that had been pre-heated to 170° C., to increase the concentration of the polymer in the solution to 70 mass %.

The resultant polymerization solution was fed into a thin-film evaporator having a heat transfer area of 0.2 m² and was subjected to devolatilization. The conditions used here were as follows: in-device temperature: 280° C., feed rate: 30 L/hr, rotational speed: 400 rpm, and degree of vacuum: 30 Torr. The polymerized product subjected to devolatilization was then pressurized using a gear pump, extruded from a strand die, cooled by water, and subsequently pelletized to obtain the methacrylic resin (B) having the N-substituted maleimide structural unit.

As a result of checking the composition of the resultant pellet polymer, the respective structural units derived from MMA, phMI, chMI, and styrene monomers were 89.8 mass %, 3.5 mass %, 5.1 mass %, and 1.6 mass %. The weight-average molecular weight was 133,000, Mz/Mw was 1.58, and Mw/Mn was 2.07. The other physical properties are listed in Table 2.

[Example 3] Production of Methacrylic Resin (C) Having N-Substituted Maleimide Structural Unit A mixed monomer solution was prepared by measuring out 500 kg of MMA, 39.6 kg of phMI, 10.4 kg of chMI, 0.275 kg of n-octylmercaptan as a chain transfer agent, and 450 kg of mXy, adding these materials into a 1.25 m³ reactor equipped with a stirring blade and a temperature controller functioning through use of a jacket, and then stirring these materials.

For the content fluid in the reactor, nitrogen bubbling was performed at a rate of 30 L/min for 1 hour. Dissolved oxygen was thus removed. After this, steam was blown into the jacket to increase the solution temperature in the reactor to 120° C. While stirring at 50 rpm, a polymerization initiator solution obtained by dissolving 0.175 kg of 1,1-di(t-butylperoxy)cyclohexane in 3.000 kg of mXy was added at a rate of 1.5 kg/hr, thus starting polymerization.

During the polymerization, the solution temperature in the reactor was controlled to 120±2° C. through temperature adjustment using the jacket. After 30 min from the start of polymerization, the addition rate of the initiator solution was decreased to 0.75 kg/hr.

The addition rate of the initiator solution was further decreased to 0.5 kg/hr after 2 hours from the start of polymerization, and to 0.2 kg/hr after 3 hours from the start of polymerization. The addition was stopped after 7 hours from the start of polymerization.

After 10 hours from the start of polymerization, a polymerization solution including methacrylic resin having a cyclic structure-containing main chain was obtained.

The one-hour half-life temperature of 1,1-di(t-butylperoxy)cyclohexane used as the initiator was 111° C., the one-minute half-life temperature was 154° C., and the half-life at the polymerization temperature of 120° C. was 24 min.

After each of 5 hours, 8 hours, and 10 hours (polymerization end) from the start of polymerization, the polymer solution was sampled, and the polymerization conversion rate was analyzed from the residual monomer concentration. The results were 85.0% after 5 hours, 93.3% after 8 hours, and 94.0% after 10 hours.

This polymerization solution was fed into a concentrating device comprising a tubular heat exchanger and a vaporization tank that had been pre-heated to 170° C., to increase the concentration of the polymer in the solution to 70 mass %.

The resultant polymerization solution was fed into a thin-film evaporator having a heat transfer area of 0.2 m² and was subjected to devolatilization. The conditions used here were as follows: in-device temperature: 280° C., feed rate: 30 L/hr, rotational speed: 400 rpm, and degree of vacuum: 30 Torr. The polymerized product subjected to devolatilization was then pressurized using a gear pump, extruded from a strand die, cooled by water, and subsequently pelletized to obtain the methacrylic resin (C) having the N-substituted maleimide structural unit.

As a result of checking the composition of the resultant pellet polymer, the respective structural units derived from MMA, phMI, and chMI monomers were 91.1 mass %, 7.3 mass %, and 1.6 mass %. The weight-average molecular weight was 151,000, Mz/Mw was 1.75, and Mw/Mn was 2.29. The other physical properties are listed in Table 2.

[Example 4] Production of Methacrylic Resin (D) Having N-Substituted Maleimide Structural Unit A mixed monomer solution was prepared by measuring out 112.5 kg of MMA, 12.5 kg of phMI, 0.50 kg of n-octylmercaptan as a chain transfer agent, and 125 kg of toluene, adding these materials into a 1.25 m³ reactor equipped with a stirring blade and a temperature controller functioning through use of a jacket, and then stirring these materials.

Next, an additional mixed monomer solution was prepared by measuring out 337.5 kg of MMA, 37.5 kg of phMI, and 375 kg of toluene, adding these materials into a tank 1, and then stirring these materials.

For the content fluid in the reactor, nitrogen bubbling was performed at a rate of 30 L/min for 1 hour. For the content fluid in the tank 1, nitrogen bubbling was performed at a rate of 10 L/min for 30 min. Dissolved oxygen was thus removed.

After this, steam was blown into the jacket to increase the solution temperature in the reactor to 110° C. While stirring at 50 rpm, a polymerization initiator solution obtained by dissolving 0.5 kg of t-butylperoxyisopropylmonocarbonate in 1 kg of toluene was added, thus starting polymerization. Further, a polymerization initiator solution obtained by dissolving 0.75 kg of t-butylperoxyisopropylmonocarbonate in 1.5 kg of toluene was added at uniform rate for 1 hour.

During the polymerization, the solution temperature in the reactor was controlled to 110±2° C. through temperature adjustment using the jacket. After 12 hours from the start of polymerization, a polymerization solution including methacrylic resin having a cyclic structure-containing main chain was obtained.

The one-hour half-life temperature of t-butylperoxyisopropylmonocarbonate used as the initiator was 118° C., and the half-life at the polymerization temperature of 110° C. was 153 min.

After each of 5.5 hours, 7 hours, 10 hours, and 12 hours (polymerization end) from the start of polymerization, the polymer solution was sampled, and the polymerization conversion rate was analyzed from the residual monomer concentration. The results were 84.2% after 5.5 hours, 90.0% after 7 hours, 95% after 10 hours, and 97.3% after 12 hours.

This polymerization solution was fed into a concentrating device comprising a tubular heat exchanger and a vaporization tank that had been pre-heated to 170° C., to increase the concentration of the polymer in the solution to 70 mass %.

The resultant polymerization solution was fed into a thin-film evaporator having a heat transfer area of 0.2 m² and was subjected to devolatilization. The conditions used here were as follows: in-device temperature: 280° C., feed rate: 30 L/hr, rotational speed: 400 rpm, and degree of vacuum: 30 Torr. The polymerized product subjected to devolatilization was then pressurized using a gear pump, extruded from a strand die, cooled by water, and subsequently pelletized to obtain the methacrylic resin (D) having the N-substituted maleimide structural unit.

As a result of checking the composition of the resultant pellet polymer, the respective structural units derived from MMA and phMI monomers were 90.1 mass % and 9.9 mass %. The weight-average molecular weight was 145,000, Mz/Mw was 1.65, and Mw/Mn was 2.16. The other physical properties are listed in Table 2.

[Example 5] Production of Methacrylic Resin (E) Having Lactone Ring Structural Unit In this case, 20 parts by mass of methyl methacrylate, 5 parts by mass of 2-(hydroxymethyl)methyl acrylate, 25 parts by mass of toluene, and 0.025 parts by mass of tris(2,4-di-t-butylphenyl)phosphite as an organic phosphorous compound were introduced into an autoclave that had been purged with nitrogen in advance, including a stirring device, a temperature sensor, a cooling pipe, and a nitrogen gas introduction pipe.

After this, while introducing nitrogen gas, the temperature was increased to 100° C. At the same time as adding 0.05 parts by mass of t-amyl peroxyisononanoate as a polymerization initiator, dropping of a toluene solution containing 0.075 parts by mass of t-amyl peroxyisononanoate was started. While dropping the toluene solution for 1.5 hours, solution polymerization was performed at about 105° C. to 110° C. under reflux. Further, polymerization was continued for 5.5 hours. Moreover, after 30 min from the start of polymerization, 20 parts by mass of methyl methacrylate, 5 parts by mass of 2-(hydroxymethyl)methyl acrylate, and 25 parts by mass of toluene were added at constant rate for 2 hours.

Next, 0.05 parts by mass of a stearyl phosphate/distearyl phosphate mixture as an organic phosphorous compound was added as a cyclization catalyst to the resultant polymer solution. Cyclization condensation reaction was performed at about 90° C. to 102° C. for 2 hours, under reflux.

The one-hour half-life temperature of t-amyl peroxyisononanoate used as the initiator was 114° C., the half-life at the polymerization temperature of 110° C. was 101 min, and the half-life at 105° C. was 180 min.

After each of 4 hours and 7.5 hours from the start of polymerization, the polymer solution was sampled, and the polymerization conversion rate was analyzed from the residual monomer concentration. The results were 84.6% after 4 hours, and 94.8% after 7.5 hours. The time average of the polymerization temperature from 0 hours to 7.5 hours from the start of polymerization was 105° C.

The resultant polymer solution was then heated to 240° C. by a heater composed of a multitubular heat exchanger, and introduced into a twin screw extruder having a plurality of vent ports for devolatilization and a plurality of side feed ports downstream. In this way, cyclization reaction was made to proceed while performing devolatilization.

In the twin screw extruder, the resultant copolymer solution was fed at 15 kg/hr in terms of resin, and the following conditions were used: barrel temperature: 250° C., rotational speed: 100 rpm, and degree of vacuum: 10 Torr to 300 Torr.

The resin composition melt-kneaded in the twin screw extruder was extruded from the strand die, water-cooled, and then pelletized to obtain a resin composition.

As a result of checking the composition of the resultant resin composition, the content of the lactone ring structural unit was 32.8 mass %. The content of the lactone ring structural unit was measured according to the method described in JP 2007-297620 A. The weight-average molecular weight was 124,000, Mz/Mw was 1.62, and Mw/Mn was 2.13. The other physical properties are listed in Table 2.

[Comparative Example 1] Production of Methacrylic Resin (F) Having N-Substituted Maleimide Structural Unit A mixed monomer solution was prepared by measuring out 445.5 kg of MMA, 44.0 kg of phMI, 60.5 kg of chMI, 0.55 kg of n-octylmercaptan as a chain transfer agent, and 450 kg of mXy, adding these materials into a 1.25 m³ reactor equipped with a stirring blade and a temperature controller functioning through use of a jacket, and then stirring these materials.

For the content fluid in the reactor, nitrogen bubbling was performed at a speed of 30 L/min for 1 hour. Dissolved oxygen was thus removed. After this, steam was blown into the jacket to increase the solution temperature in the reactor to 130° C. While stirring at 50 rpm, a polymerization initiator solution obtained by dissolving 1.10 kg of t-butylperoxy-2-ethylhexanoate in 4.9 kg of mXy was added at a speed of 1 kg/hr for 6 hours, thus starting polymerization.

During the polymerization, the solution temperature in the reactor was controlled to 130±2° C. through temperature adjustment using the jacket. After 8 hours from the start of polymerization, a polymerization solution including methacrylic resin having a cyclic structure-containing main chain was obtained.

The one-hour half-life temperature of t-butylperoxy-2-ethylhexanoate used as the initiator was 92° C., the one-minute half-life temperature was 134° C., and the half-life at the polymerization temperature of 130° C. was 1.4 min.

After each of 3.3 hours, 6 hours, and 8 hours (polymerization end) from the start of polymerization, the polymer solution was sampled, and the polymerization conversion rate was analyzed from the residual monomer concentration. The results were 84.9% after 3.3 hours, 96.7% after 6 hours, and 96.8% after 8 hours.

This polymerization solution was fed into a concentrating device comprising a tubular heat exchanger and a vaporization tank that had been pre-heated to 170° C., to increase the concentration of the polymer in the solution to 70 mass %.

The resultant polymerization solution was fed into a thin-film evaporator having a heat transfer area of 0.2 $m^2$ and was subjected to devolatilization. The conditions used here were as follows: in-device temperature: 280° C., feed rate: 30 L/hr, rotational speed: 400 rpm, and degree of vacuum: 30 Torr. The polymerized product subjected to devolatilization was then pressurized using a gear pump, extruded from a strand die, cooled by water, and subsequently pelletized to obtain the methacrylic resin (F) having the N-substituted maleimide structural unit.

As a result of checking the composition of the resultant pellet polymer, the respective structural units derived from MMA, phMI, and chMI monomers were 81.3 mass %, 7.7 mass %, and 11 mass %. The weight-average molecular weight was 143,000, Mz/Mw was 1.85, and Mw/Mn was 2.75. The other physical properties are listed in Table 2.

[Comparative Example 2] Production of Methacrylic Resin (G) Having N-Substituted Maleimide Structural Unit A mixed monomer solution was prepared by measuring out 450.0 kg of MMA, 50.0 kg of phMI, 0.50 kg of n-dodecylmercaptan as a chain transfer agent, and 500 kg of toluene, adding these materials into a 1.25 $m^3$ reactor equipped with a stirring blade and a temperature controller functioning through use of a jacket, and then stirring these materials.

For the content fluid in the reactor, nitrogen bubbling was performed at a rate of 30 L/min for 1 hour. Dissolved oxygen was thus removed. After this, steam was blown into the jacket to increase the solution temperature in the reactor to 110° C. While stirring at 50 rpm, a polymerization initiator solution obtained by dissolving 1.50 kg of t-butylperoxyisopropylmonocarbonate in 4.5 kg of toluene was added into the reactor, thus starting polymerization.

During the polymerization, the solution temperature in the reactor was controlled to 110±2° C. through temperature adjustment using the jacket. After 12 hours from the start of polymerization, a polymerization solution including methacrylic resin having a cyclic structure-containing main chain was obtained.

The one-hour half-life temperature of t-butylperoxyisopropylmonocarbonate used as the initiator was 118° C., and the half-life at the polymerization temperature of 110° C. was 153 min.

After each of 4 hours, 8 hours, and 12 hours (polymerization end) from the start of polymerization, the polymer solution was sampled, and the polymerization conversion rate was analyzed from the residual monomer concentration. The results were 90.4% after 4 hours, 96.5% after 8 hours, and 98.0% after 12 hours.

This polymerization solution was fed into a concentrating device comprising a tubular heat exchanger and a vaporization tank that had been pre-heated to 170° C., to increase the concentration of the polymer in the solution to 70 mass %.

The resultant polymerization solution was fed into a thin-film evaporator having a heat transfer area of 0.2 $m^2$ and was subjected to devolatilization. The conditions used here were as follows: in-device temperature: 280° C., feed rate: 30 L/hr, rotational speed: 400 rpm, and degree of vacuum: 30 Torr. The polymerized product subjected to devolatilization was then pressurized using a gear pump, extruded from a strand die, cooled by water, and subsequently pelletized to obtain the methacrylic resin (G) having the N-substituted maleimide structural unit.

As a result of checking the composition of the resultant pellet polymer, the respective structural units derived from MMA and phMI monomers were 90.3 mass % and 9.7 mass %. The weight-average molecular weight was 155,000, Mz/Mw was 1.82, and Mw/Mn was 2.63. The other physical properties are listed in Table 2.

[Comparative Example 3] Production of Methacrylic Resin (H) Having N-Substituted Maleimide Structural Unit A mixed monomer solution was prepared by measuring out 140.0 kg of MMA, 100.0 kg of chMI, and 250 kg of toluene were measured, adding these materials into a 1.25 $m^3$ reactor equipped with a stirring blade and a temperature controller functioning through use of a jacket, and then stirring these materials.

Next, an additional mixed monomer solution was prepared by measuring out 82.5 kg of MMA, 25.0 kg of chMI, 35.0 kg of styrene, and 200.0 kg of toluene, adding these materials into a tank 1, and then stirring these materials.

Further, an additional mixed monomer solution was prepared by measuring out 82.5 kg of MMA, 35.0 kg of styrene, and 50.0 kg of toluene, adding these materials into a tank 2, and then stirring these materials.

For the content fluid in the reactor, nitrogen bubbling was performed at a rate of 30 L/min for 1 hour. For the content fluid in each of the tanks 1 and 2, nitrogen bubbling was performed at a rate of 10 L/min for 30 min. Dissolved oxygen was thus removed.

After this, steam was blown into the jacket to increase the solution temperature in the reactor to 110° C. While stirring at 50 rpm, a polymerization initiator solution obtained by dissolving 0.20 kg of t-butylperoxyisopropylmonocarbonate in 0.8 kg of toluene was added into the reactor, thus starting polymerization. Moreover, a polymerization initiator solution obtained by dissolving 2.30 kg of t-butylperoxyisopropylmonocarbonate in 4.70 kg of toluene was added at a rate of 2 kg/hr for 3.5 hours.

For 3.5 hours from the start of polymerization, the content fluid in the tank 1 was added at constant rate. For 3.5 hours after this, the content fluid in the tank 2 was added at constant rate.

During the polymerization, the solution temperature in the reactor was controlled to 110±2° C. through temperature adjustment using the jacket. After 10 hours from the start of polymerization, a polymerization solution including methacrylic resin having a cyclic structure-containing main chain was obtained.

The one-hour half-life temperature of t-butylperoxyisopropylmonocarbonate used as the initiator was 118° C., and the half-life at the polymerization temperature of 110° C. was 153 min.

After each of 7 hours and 10 hours (polymerization end) from the start of polymerization, the polymer solution was sampled, and the polymerization conversion rate was analyzed from the residual monomer concentration. The results were 90.1% after 7 hours, and 97.3% after 10 hours.

This polymerization solution was fed into a concentrating device comprising a tubular heat exchanger and a vaporization tank that had been pre-heated to 170° C., to increase the concentration of the polymer in the solution to 70 mass %.

The resultant polymerization solution was fed into a thin-film evaporator having a heat transfer area of 0.2 m$^2$ and was subjected to devolatilization. The conditions used here were as follows: in-device temperature: 280° C., feed rate: 30 L/hr, rotational speed: 400 rpm, and degree of vacuum: 30 Torr. The polymerized product subjected to devolatilization was then pressurized using a gear pump, extruded from a strand die, cooled by water, and subsequently pelletized to obtain the methacrylic resin (H) having the N-substituted maleimide structural unit.

As a result of checking the composition of the resultant pellet polymer, the respective structural units derived from MMA, chMI, and styrene monomers were 60.3 mass %, 25.5 mass %, and 14.2 mass %. The weight-average molecular weight was 102,000, Mz/Mw was 1.90, and Mw/Mn was 2.84. The other physical properties are listed in Table 2.

[Comparative Example 4] Production of Methacrylic Resin (I) Having Lactone Ring Structural Unit In this case, 40 parts by mass of methyl methacrylate, 10 parts by mass of 2-(hydroxymethyl)methyl acrylate, 50 parts by mass of toluene, and 0.025 parts by mass of tris(2,4-di-t-butylphenyl)phosphite as an organic phosphorous compound were introduced into an autoclave that had been purged with nitrogen in advance, including a stirring device, a temperature sensor, a cooling pipe, and a nitrogen gas introduction pipe.

After this, while introducing nitrogen gas, the temperature was increased to 100° C. At the same time as adding 0.05 parts by mass of t-amyl peroxyisononanoate as a polymerization initiator, dropping of a toluene solution containing 0.1 parts by mass of t-amyl peroxyisononanoate was started. While dropping the toluene solution for 2 hours, solution polymerization was performed at about 105° C. to 110° C. under reflux. Further, polymerization was continued for 4 hours.

Next, 0.05 parts by mass of a stearyl phosphate/distearyl phosphate mixture as an organic phosphorous compound was added as a cyclization catalyst to the resultant polymer solution. Cyclization condensation reaction was performed at about 90° C. to 102° C. for 2 hours, under reflux.

The one-hour half-life temperature of t-amyl peroxyisononanoate used as the initiator was 114° C., the half-life at the polymerization temperature of 110° C. was 101 min, and the half-life at 105° C. was 180 min.

After each of 4 hours and 6 hours from the start of polymerization, the polymer solution was sampled, and the polymerization conversion rate was analyzed from the residual monomer concentration. The results were 89.8% after 4 hours, and 95.2% after 6 hours.

The resultant polymer solution was then heated to 240° C. by a heater composed of a multitubular heat exchanger, and introduced into a twin screw extruder having a plurality of vent ports for devolatilization and a plurality of side feed ports downstream. In this way, cyclization reaction was made to proceed while performing devolatilization.

In the twin screw extruder, the resultant copolymer solution was fed at 15 kg/hr in terms of resin, and the following conditions were used: barrel temperature: 250° C., rotational speed: 100 rpm, and degree of vacuum: 10 Torr to 300 Torr.

The resin composition melt-kneaded in the twin screw extruder was extruded from the strand die, water-cooled, and then pelletized to obtain a resin composition.

As a result of checking the composition of the resultant resin composition, the content of the lactone ring structural unit was 31.5 mass %. The content of the lactone ring structural unit was measured according to the method described in JP 2007-297620 A. The weight-average molecular weight was 121,000, Mz/Mw was 1.78, and Mw/Mn was 2.52. The other physical properties are listed in Table 2.

TABLE 2

|  |  |  |  |  | Example 1 | Example 2 | Example 3 | Example 4 | Example 5 |
|---|---|---|---|---|---|---|---|---|---|
| Methacrylic resin production method | Polymerization method |  |  |  | First polymerization method | First polymerization method | First polymerization method | Second polymerization method | Second polymerization method |
|  | Polymerization temperature |  |  | [° C.] | 124 | 124 | 120 | 110 | 105 |
|  | Initiator | Type |  | [—] | PHC | PHHC | PHC | PBI | L570 |
|  |  | Half-life |  | [mm.] | 16 | 11 | 24 | 153 | 180 |
|  | 1 | Polymerization conversion rate |  | [%] | 4 h 84.8<br>6 h 93.3<br>8 h 95.7<br>10 h 96 | 4 h 84.5<br>6 h 92.2<br>8 h 95.2<br>10 h 95.5 | 5 h 85<br>8 h 93.3<br>10 h 94 | 5.5 h 84.2<br>7 h 90<br>10 h 95<br>12 h 97.3 | 4 h 84.6<br>6 h 93.1<br>8 h 95.5<br>9 h 97 |
|  | 3 | Molecular weight | Mz [ten thousand] | [—] | 21.7 | 21 | 26.4 | 23.9 | 20.1 |
|  |  |  | Mw [ten thousand] | [—] | 14.1 | 13.3 | 15.1 | 14.5 | 12.4 |
|  |  |  | Mn [ten thousand] | [—] | 7.3 | 6.4 | 6.6 | 6.7 | 5.8 |
|  |  |  | Mz/Mw | [—] | 1.54 | 1.58 | 1.75 | 1.65 | 1.62 |
|  |  |  | Mw/Mn | [—] | 1.94 | 2.07 | 2.29 | 2.16 | 2.13 |
|  | 4 | Tg |  | [° C.] | 135 | 123 | 128 | 129 | 129 |
|  | 5 | $C_p$ |  | [Pa$^{-1}$] | $0.2 \times 10^{-12}$ | $1.4 \times 10^{-12}$ | $0.9 \times 10^{-12}$ | $0.5 \times 10^{-12}$ | $2.0 \times 10^{-12}$ |
|  | 6 | Soluble content |  | [mass %] | 1.8 | 2.1 | 2.5 | 3.8 | 4.2 |
|  | 7 | Iasolule content | 680 nm | [Y]<br>[%] | 3.8<br>92.1 | 3.5<br>91.5 | 5.2<br>91.8 | 4.5<br>91.2 | 4.2<br>91.2 |

TABLE 2-continued

|  |  |  |  | Comparative Example 1 | Comparative Example 2 | Comparative Example 3 | Comparative Example 4 |
|---|---|---|---|---|---|---|---|
| | 8 | Film formation stain | [—] | Poor | Poor | Good | Good |

| Methacrylic resin production method | Polymerization method | | | First polymerization method | Second polymerization method | Second polymerization method | Second polymerization method |
|---|---|---|---|---|---|---|---|
| | Polymerization temperature | | [° C.] | 130 | 110 | 110 | 105 |
| | Initiator | Type | [—] | PHO | PBI | PBI | L570 |
| | | Half-life | [mm.] | 1.4 | 153 | 153 | 180 |
| | 1 | Polymerization conversion rate | [%] | 3.3 h  84.9<br>4 h  90.1<br>6 h  96.7<br>8 h  96.8 | 4 h  90.4<br>8 h  96.5<br>12 h  98 | 7 h  90.1<br>10 h  97.3<br>12 h  98.4 | 4 h  89.8<br>6 h  95.2<br>8 h  97 |
| | 3  Molecular weight | Mz [ten thousand] | [—] | 26.5 | 28.2 | 19.4 | 21.5 |
| | | Mw [ten thousand] | [—] | 14.3 | 15.5 | 10.2 | 12.1 |
| | | Mn [ten thousand] | [—] | 5.2 | 5.9 | 3.58 | 4.8 |
| | | Mz/Mw | [—] | 1.85 | 1.82 | 1.9 | 1.78 |
| | | Mw/Mn | [—] | 2.75 | 2.63 | 2.84 | 2.52 |
| | 4 | Tg | [° C.] | 135 | 128 | 133 | 129 |
| | 5 | $C_p$ | [Pa$^{-1}$] | $0.2 \times 10^{-12}$ | $0.5 \times 10^{-12}$ | $2.5 \times 10^{-12}$ | $2.2 \times 10^{-12}$ |
| | 6 | Soluble content | [mass %] | 8.3 | 7.2 | 6.8 | 9.8 |
| | 7  Iasolule content | [Y] | [—] | 8.3 | 8.8 | 4.7 | 7.9 |
| | | 680 nm transmittance | [%] | 91.5 | 91.4 | 88.5 | 90.7 |
| | 8 | Film formation stain | [—] | Poor | Poor | Good | Good |

(Note)
PHC: 1,1-di(t-butylperoxy)cyclohexane
PHHC: 1,1-di(t-hexylperoxy)cyclohexane
PBI: t-butylperoxyisopropylmonocarbonate
L570: t-amylperoxyisononanoate
PBO: t-butylperoxy-2-ethylhexanoate

INDUSTRIAL APPLICABILITY

The methacrylic resin according to this disclosure has high heat resistance, highly controlled birefringence, excellent color tone and transparency, and excellent moldability.

The methacrylic resin according to this disclosure can be suitably used as optical material such as: a polarizing plate protection film used in a display such as a liquid crystal display, a plasma display, an organic EL display, a field emission display, or a rear projection television; a phase difference plate (retarder) such as a ¼ wavelength plate or a ½ wavelength plate; a liquid crystal optical compensation film such as a viewing angle control film; a display front plate; a display substrate; a lens; a transparent conductive substrate such as a transparent substrate used in a solar cell or a touch panel; a waveguide, a lens, a lens array, an optical fiber, or an optical fiber covering material in the fields of optical communication systems, optical switching systems, and optical measurement systems; an LED lens; and a lens cover.

The invention claimed is:

1. A methacrylic resin composition consisting essentially of a methacrylic resin, the methacrylic resin comprising
a structural unit (B) having a cyclic structure-containing main chain, the structural unit (B) including at least one structural unit selected from the group consisting of an N-substituted maleimide-based structural unit (B-1) and a lactone ring structural unit (B-2), wherein
a glass transition temperature of the methacrylic resin is more than 120° C. and 160° C. or less,
an amount of a methanol-soluble content is 5 mass % or less relative to 100 mass % of a total amount of the methanol-soluble content and a methanol-insoluble content in the methacrylic resin, and
an yellowness index YI measured using a 10 cm optical path length cell for a 20 w/v % chloroform solution of the methanol-insoluble content of the methacrylic resin is 0 to 7.

2. The methacrylic resin composition according to claim 1, wherein
a transmittance in 680 nm as measured using the 10 cm optical path length cell for the 20 w/v % chloroform solution of the methanol-insoluble content is 90% or more.

3. The methacrylic resin composition according to claim 1, wherein the methacrylic resin comprises 50 mass % to 97 mass % of a methacrylic acid ester monomer unit (A), relative to 100 mass % of the methacrylic resin.

4. The methacrylic resin composition according to claim 1, wherein
the methacrylic resin comprises 3 mass % to 30 mass % of the structural unit (B) having a cyclic structure-containing main chain, and 0 mass % to 20 mass % of an other vinyl-based monomer unit (C) copolymerizable with a methacrylic acid ester monomer, relative to 100 mass % of the methacrylic resin.

5. The methacrylic resin composition according to claim 4, wherein
the structural unit (B) is contained in an amount of 45 mass % to 100 mass % relative to 100 mass %, in total, of the structural unit (B) and the monomer unit (C).

6. The methacrylic resin composition according to claim 4, wherein
the monomer unit (C) includes at least one structural unit selected from the group consisting of an acrylic acid ester monomer, an aromatic vinyl-based monomer, and a vinyl cyanide-based monomer.

7. The methacrylic resin composition according to claim 1, wherein the methacrylic resin has a photoelastic coefficient of $-2 \times 10^{-12}$ $Pa^{-1}$ to $+2 \times 10^{-12}$ $Pa^{-1}$.

8. The methacrylic resin composition according to claim 1, wherein the methacrylic resin has a ratio Mz/Mw of a Z-average molecular weight Mz to a weight-average molecular weight Mw of 1.3 to 2.0 as measured by gel permeation chromatography (GPC).

9. The methacrylic resin composition according to claim 2, wherein the methacrylic resin comprises 50 mass % to 97 mass % of a methacrylic acid ester monomer unit (A), relative to 100 mass % of the methacrylic resin.

10. The methacrylic resin composition according to claim 2, wherein the methacrylic resin has a photoelastic coefficient of $-2 \times 10^{-12}$ $Pa^{-1}$ to $+2 \times 10^{-12}$ $Pa^{-1}$.

11. The methacrylic resin composition according to claim 2, wherein the methacrylic resin has a ratio Mz/Mw of a Z-average molecular weight Mz to a weight-average molecular weight Mw of 1.3 to 2.0 as measured by gel permeation chromatography (GPC).

12. The methacrylic resin composition according to claim 3, wherein the methacrylic resin has a photoelastic coefficient of $-2 \times 10^{-12}$ $Pa^{-1}$ to $+2 \times 10^{-12}$ $Pa^{-1}$.

13. The methacrylic resin composition according to claim 3, wherein the methacrylic resin has a ratio Mz/Mw of a Z-average molecular weight Mz to a weight-average molecular weight Mw of 1.3 to 2.0 as measured by gel permeation chromatography (GPC).

14. The methacrylic resin composition according to claim 7, wherein the methacrylic resin has a ratio Mz/Mw of a Z-average molecular weight Mz to a weight-average molecular weight Mw of 1.3 to 2.0 as measured by gel permeation chromatography (GPC).

15. The methacrylic resin composition according to claim 10, wherein the methacrylic resin has a ratio Mz/Mw of a Z-average molecular weight Mz to a weight-average molecular weight Mw of 1.3 to 2.0 as measured by gel permeation chromatography (GPC).

16. The methacrylic resin composition according to claim 9, wherein the methacrylic resin has a photoelastic coefficient of $-2 \times 10^{-12}$ $Pa^{-1}$ to $+2 \times 10^{-12}$ $Pa^{-1}$.

17. The methacrylic resin composition according to claim 16, wherein the methacrylic resin has a ratio Mz/Mw of a Z-average molecular weight Mz to a weight-average molecular weight Mw of 1.3 to 2.0 as measured by gel permeation chromatography (GPC).

* * * * *

UNITED STATES PATENT AND TRADEMARK OFFICE
CERTIFICATE OF CORRECTION

PATENT NO. : 10,174,145 B1
APPLICATION NO. : 15/880480
DATED : January 8, 2019
INVENTOR(S) : Junichi Yoshida et al.

Page 1 of 1

It is certified that error appears in the above-identified patent and that said Letters Patent is hereby corrected as shown below:

On the Title Page

Under the item (56) Reference Cited, please make the correction as shown below:
In FOREIGN PATENT DOCUMENTS, please delete "H109151218" and insert --H09151218--.
In FOREIGN PATENT DOCUMENTS, please delete "H109324016" and insert --H09324016--.

Signed and Sealed this
Ninth Day of April, 2019

Andrei Iancu
*Director of the United States Patent and Trademark Office*